United States Patent [19]

Kosa et al.

[11] Patent Number: 5,335,305
[45] Date of Patent: Aug. 2, 1994

[54] OPTICAL SENSOR FOR FLUID PARAMETERS

[75] Inventors: Nadhir B. Kosa, The Woodlands; Gene J. Twiggs, Magnolia; James R. Salter; Raghuvir Singh, both of The Woodlands; David J. Costello, Spring; Leslie A. Schlain, Woodlands, all of Tex.

[73] Assignee: OPtex Biomedical, Inc., The Woodlands, Tex.

[21] Appl. No.: 965,232

[22] Filed: Oct. 23, 1992

Related U.S. Application Data

[63] Continuation-in-part of Ser. No. 810,479, Dec. 19, 1991, abandoned.

[51] Int. Cl.$^5$ .............................................. G02B 6/38
[52] U.S. Cl. ................................... 385/147; 156/154; 422/82.06; 128/634; 436/172
[58] Field of Search .................... 385/59, 12, 147, 60; 128/634; 422/58, 82.07, 82.06; 436/172

[56] References Cited

U.S. PATENT DOCUMENTS

| | | | |
|---|---|---|---|
| 3,068,742 | 12/1962 | Hicks et al. | 128/634 |
| 3,123,066 | 3/1964 | Brumley | 128/634 |
| 3,674,013 | 6/1972 | Polanyi | 128/2.05 D |
| 3,814,081 | 6/1974 | Mori | 128/634 |
| 3,904,373 | 9/1975 | Harper | 23/253 TP |
| 4,003,707 | 1/1977 | Lubbers et al. | 436/172 |
| 4,200,110 | 4/1980 | Peterson et al. | 128/634 |
| 4,306,877 | 12/1981 | Lubbers | 436/166 |
| 4,344,438 | 8/1982 | Schultz | 128/634 |
| 4,474,183 | 10/1984 | Yano et al. | 128/635 |
| 4,476,870 | 10/1984 | Peterson et al. | 128/634 |
| 4,516,022 | 5/1985 | Linógres | 250/227 |
| 4,648,892 | 3/1987 | Kittrell et al. | 65/4.21 |
| 4,669,467 | 6/1987 | Willett et al. | 128/303.1 |
| 4,682,895 | 6/1987 | Costello | 356/402 |
| 4,727,730 | 3/1988 | Boiarski et al. | 128/667 |
| 4,752,115 | 6/1988 | Murray, Jr. et al. | 350/96.29 |
| 4,758,298 | 7/1988 | Goorsky et al. | 156/296 |
| 4,785,814 | 11/1988 | Kane | 128/634 |
| 4,798,738 | 1/1989 | Yafuso et al. | 427/2 |
| 4,824,789 | 4/1989 | Yafuso et al. | 436/68 |
| 4,830,013 | 5/1989 | Maxwell | 128/637 |
| 4,889,407 | 12/1989 | Markle et al. | 350/96.29 |
| 4,907,857 | 3/1990 | Giuliani et al. | 350/96.29 |
| 4,919,891 | 4/1990 | Yafuso et al. | 422/58 |
| 4,925,268 | 5/1990 | Iyer et al. | 350/96.29 |
| 4,974,592 | 12/1990 | Branco | 128/635 |
| 4,974,929 | 12/1990 | Curry | 350/96.29 |

(List continued on next page.)

FOREIGN PATENT DOCUMENTS

| | | |
|---|---|---|
| 0073558A | 6/1982 | European Pat. Off. . |
| 0126600A | 5/1984 | European Pat. Off. . |
| 0352610 | 7/1989 | European Pat. Off. . |
| 55-37934 | 3/1980 | Japan . |
| 0124036 | 9/1981 | Japan . |
| 0154340 | 9/1984 | Japan . |
| 1525989 | 9/1978 | United Kingdom . |

OTHER PUBLICATIONS

"Progress in the Development of a Fluorescent Intravascular Blood Gas System in Man" Journal of Clinical Monitoring, pp. 147–160, vol. 6, No. 2, Apr. 1990.
"Eximer Laser Micro-Machining XLR-200 System," Image Systems, Inc. 1989.

(List continued on next page.)

*Primary Examiner*—Akm E. Ullah
*Attorney, Agent, or Firm*—Guy McClung

[57] ABSTRACT

Methods for making optical fiber sensor probes for measuring or monitoring parameters of fluids, including but not limited to measuring blood gas concentrations and pH either in a vessel in vitro or in a human artery. Such probes, in one aspect, have one or more optical fibers with one or more chambers with a chemical indicating material therein which changes in response to light transmitted therethrough. In one aspect such probes have a probe body including a plurality of fibers having a substantial portion of their surfaces covered with an opaque material to enhance light signal transmission therethrough. Such probes may also have a coating thereon of an anti-thrombogenic mnaterial.

22 Claims, 14 Drawing Sheets

U.S. PATENT DOCUMENTS

| | | | |
|---|---|---|---|
| 4,989,606 | 2/1991 | Gehrich et al. | 128/637 |
| 4,991,590 | 2/1991 | Shi | 128/667 |
| 4,999,306 | 3/1991 | Yafuso et al. | 436/68 |
| 5,000,901 | 3/1991 | Iyer et al. | 264/299 |
| 5,005,576 | 4/1991 | Gunther | 128/634 |
| 5,006,314 | 4/1991 | Gourley et al. | 422/82.07 |
| 5,009,655 | 4/1991 | Daignault et al. | 606/7 |
| 5,012,809 | 5/1991 | Shulze | 128/634 |
| 5,026,357 | 6/1991 | Leckrone | 606/7 |
| 5,044,723 | 9/1991 | MacDonald | 385/12 |
| 5,054,882 | 10/1991 | Riccitelli et al. | 385/12 |
| 5,061,857 | 10/1991 | Thompson et al. | 250/458.1 |
| 5,078,711 | 1/1992 | Kakami et al. | 606/16 |
| 5,094,959 | 3/1992 | Allen et al. | 436/172 |
| 5,098,659 | 3/1992 | Yim et al. | 422/82.07 |
| 5,102,625 | 4/1992 | Milo | 422/82.07 |
| 5,115,811 | 5/1992 | Hartlaub et al. | 128/634 |
| 5,124,130 | 6/1992 | Costello | 422/82.06 |
| 5,133,032 | 7/1992 | Salter et al. | 385/60 |
| 5,159,654 | 10/1992 | Salter | 385/59 |

OTHER PUBLICATIONS

"Instrumentation" R. Dessy, Analytical chemistry, vol. 61, No. 19, Oct. 1, 1989, pp. 1079A–1094A.

"Physiological pH Fiber–Optic Chemical Sensor Based On Energy Transfer," D. Jordan et al., American Chemical Society, 1987.

"Fiberoptic Sensors Evolve Into Medical Products," M. Moretti, Laser Focus/Electro–Optics, May 1987, pp. 118, 120.

"Measurement of Tumor pH During Microwave Induced Experimental and Clinical Hyperthermia With A Fiber Optic pH Measurement System," Van De Merwe, et al., I.J. Radiation Oncology, Jan. 1990.

"Fluorescence Analysis, A Practical Approach," White et al., pp. 102–115, 298–305, 1970.

"Oxygen Quenching of Pyrenebutyric Acid Fluorescense in Water. A Dynamic Probe of the Microenvironment," W. M. Vaughan et al., Biochemistry, vol. 9, No. 3, Feb. 3, 1970, pp. 464–473.

"Fiber Optic Chemical Sensors—A View From the Past To the Future," J. Peterson, IEEE/NSF Symposium On Biosensors–1984, pp. 35–38.

"Chemical Sensing By Evanescent Field Absorption: The Sensitivity of Optical Waveguides," Stewart et al., SPIE, vol. 990 (1988).

"Novel Techniques and Materials For Fiber Optic Chemical Sensing," Wolfbeis, Springer Proceedings In Physics, vol. 44, 1989.

"Chemical Sensors Based On Fiber Optics," Seitz, Analytical Chemistry, vol. 56, No. 1, Jan. 1984.

"Fibre Optics For Chemical Sensing," Narayanaswamy, Analytical Proceedings, vol. 22, Jul. 1985.

"Fiber Optical Fluorosensor For Determination of Halothane and/or Oxygen," Walfbeis, et al., Analytical Chemistry, vol. 57, 1985.

"Excimer Lasers: An Emerging Technology In Materials Processing," Znotins, et al., Laser Focus/Electro–Optics, May 1987.

"Fluorescence Optical Sensors For Continuous Determination of Near Neutral pH Values," Offenbacher, et al. Sensors and Actuators, vol. 9 (1986).

"Progress in the Development of a Fluorescent Intravascular Blood Gas System in Man," 1989, C. Kees Mahutte et al.

"A Fiber–Optic pH Sensor Using Acid–Base Indicators Covalently Bound on Controlled Pore Glass", Baldini et al., SPIE Proceedings, vol. 1587 (1991).

"Reusable Glass–Bound pH Indicators", Harper, Analytical Chemistry, vol. 47 (1975).

"Continuous Atrterial Blood Gas Monitoring in Rabbits: An Efficient Method for Evaluation of Ratio Based Optrodes", Martin et al., SPIE, vol. 1648 (1992).

"Design and Applications of Highly Luminescent Transition Metal Complexes", Demas and DeGraff, Analytical Chemistry, vol. 63, (1991).

"Biologically Inert Synthetic Dural Substitutes", by Sakas et al., J. Neurosurg, vol. 73 (1990).

"Determination of Oxygen Concentration by Luminescence Quenching of a Polymer–Immobilized Transition–Metal Complex", Demas et al., Analytical Chemistry, vol. 59 (1987).

"Photophysics and Photochemistry of Oxygen Sensors Based on Luminescent Transition–Metal Complexes", Demas et al., Analytical Chemistry, vol. 63 (1991).

"Fiber Optic pH for Physiological Use", Peterson et al., Analytical Chemistry vol. 52 (1980).

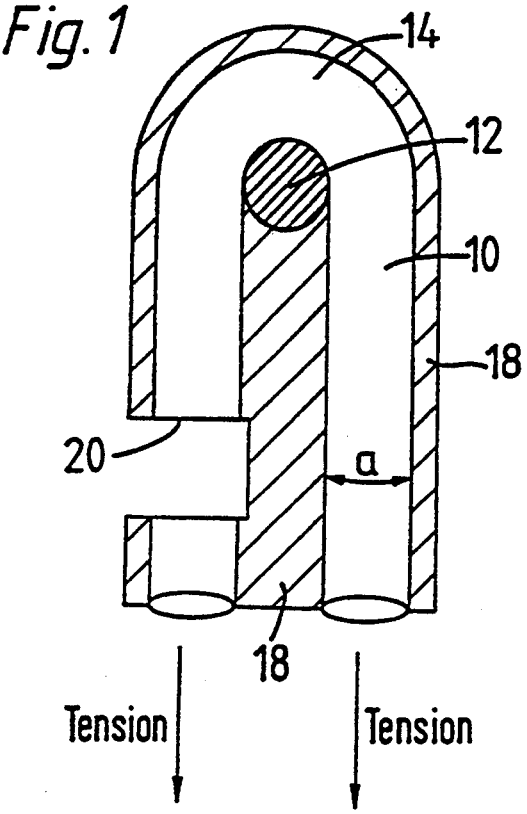
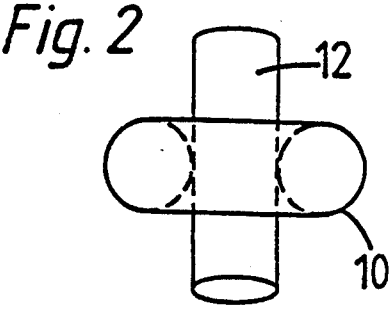
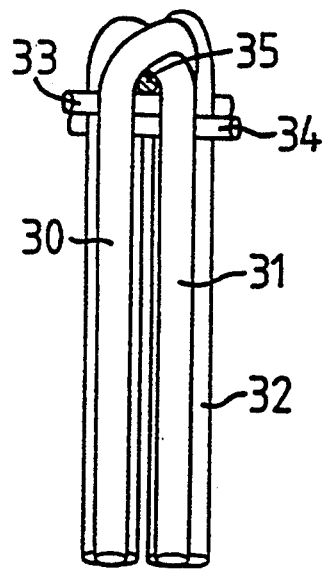
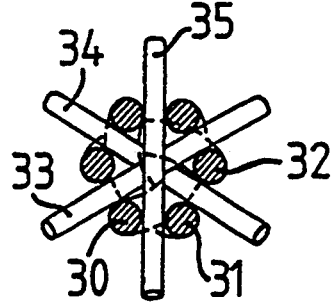
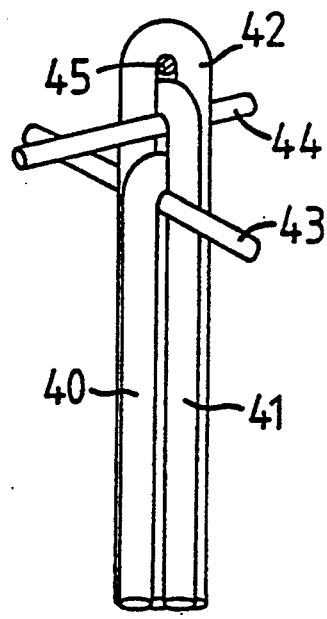
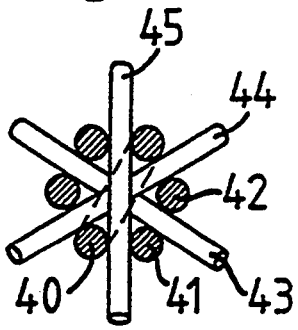

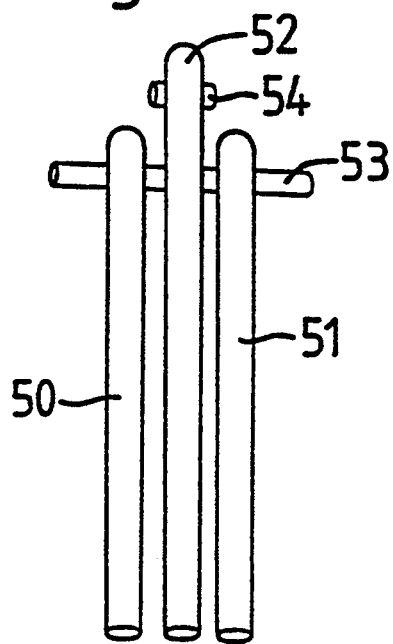
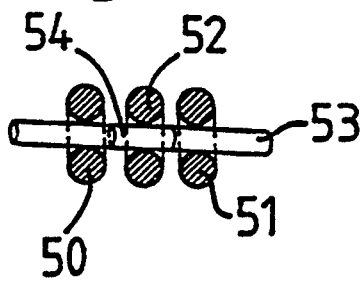
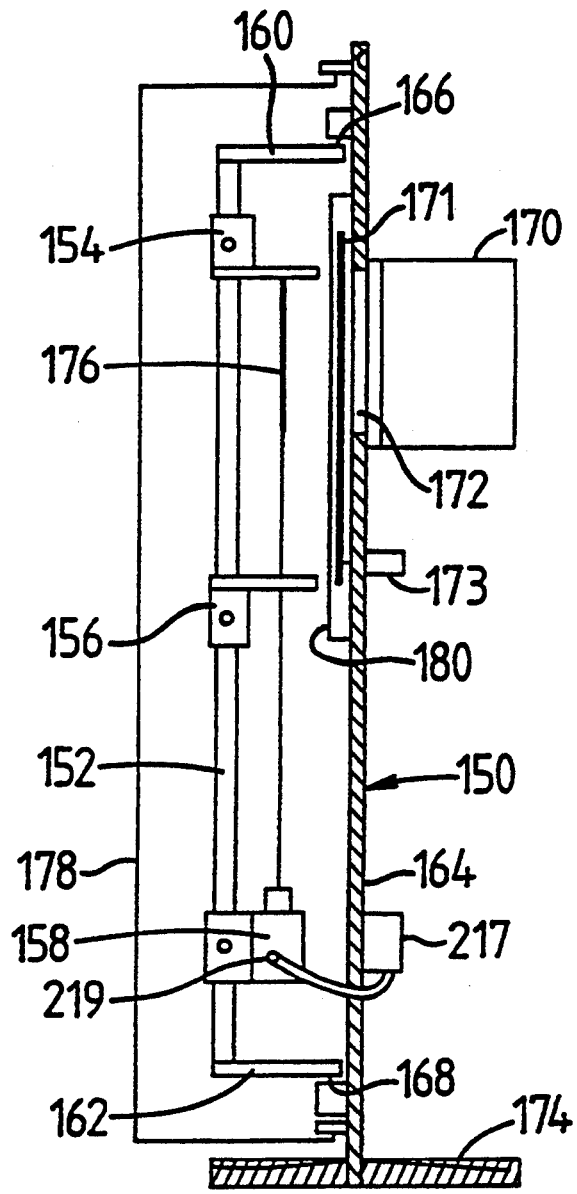

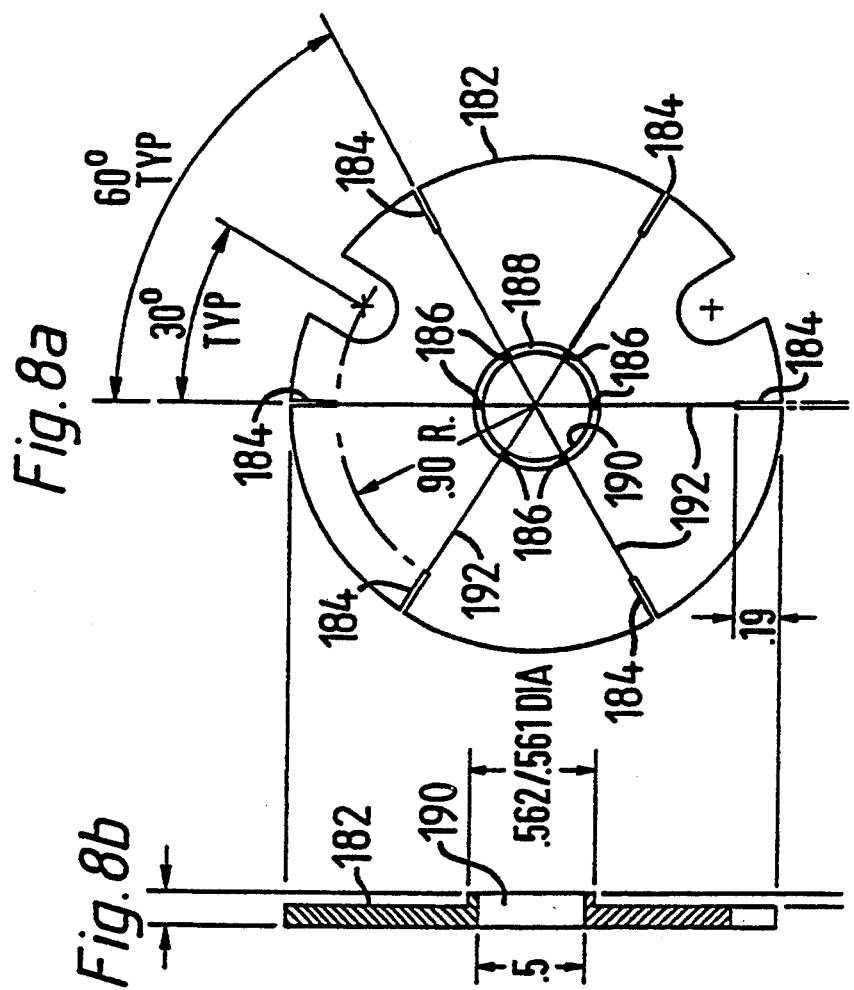
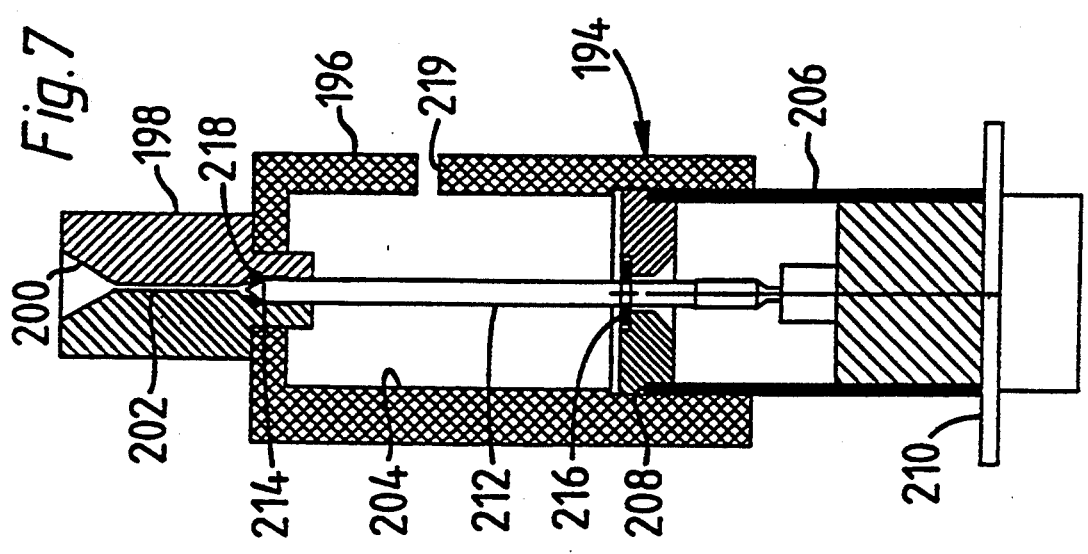

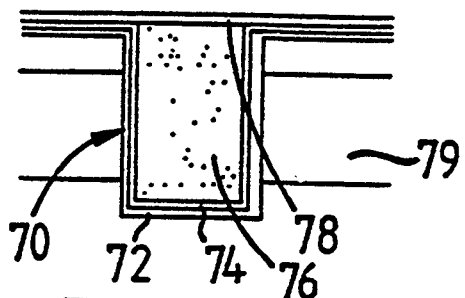
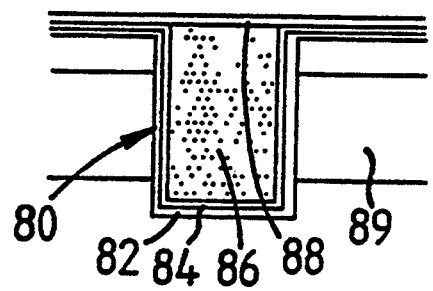
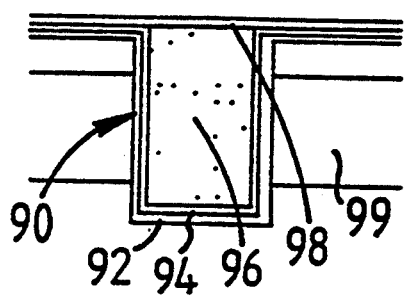
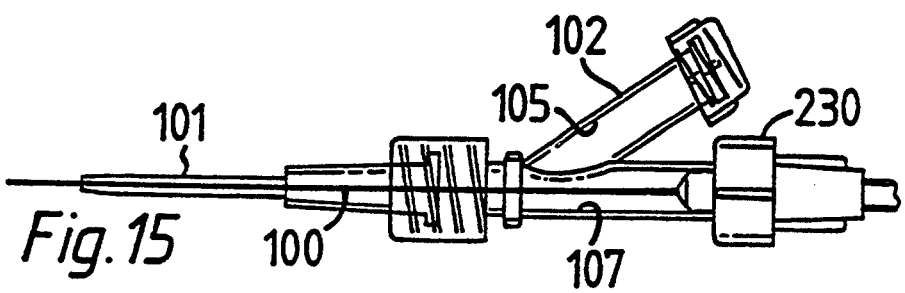
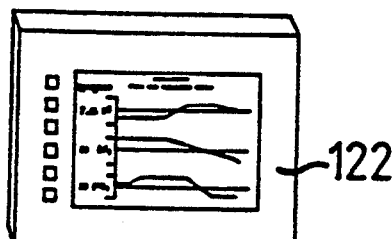
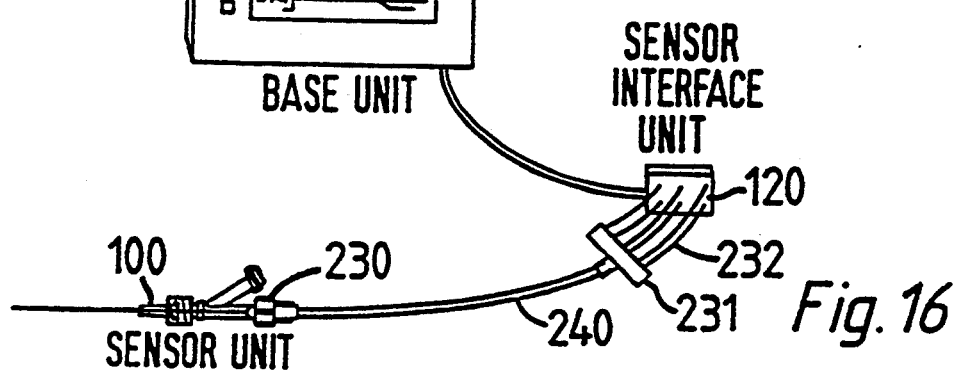

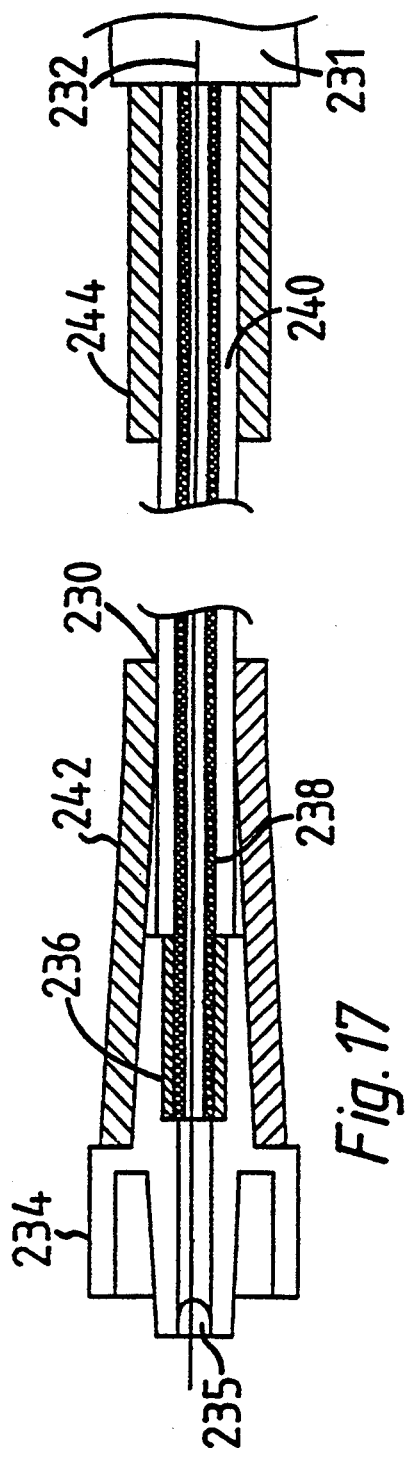
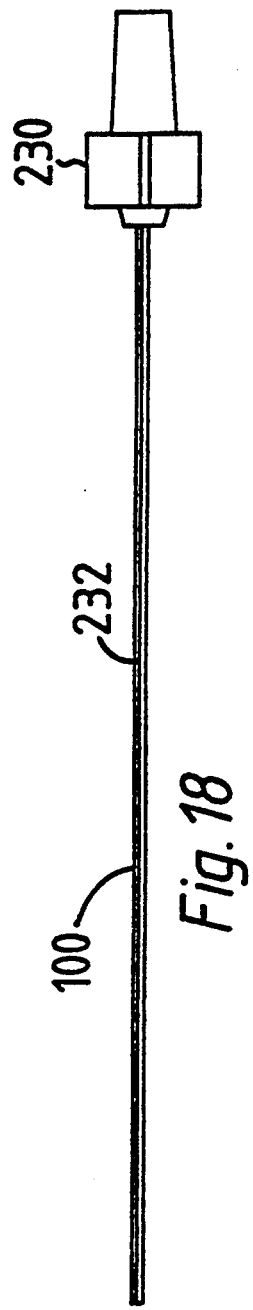
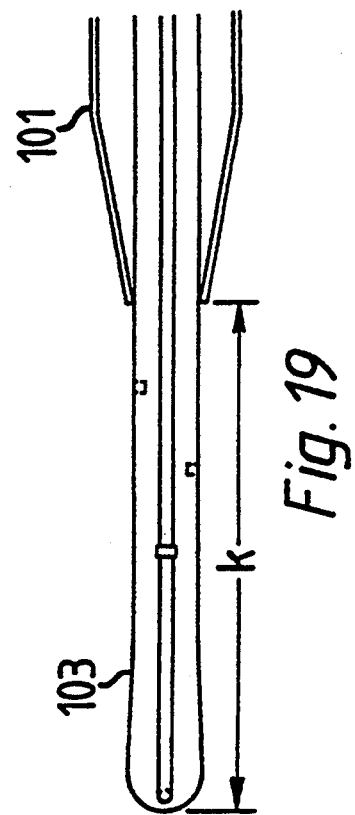
Fig. 17
Fig. 18
Fig. 19

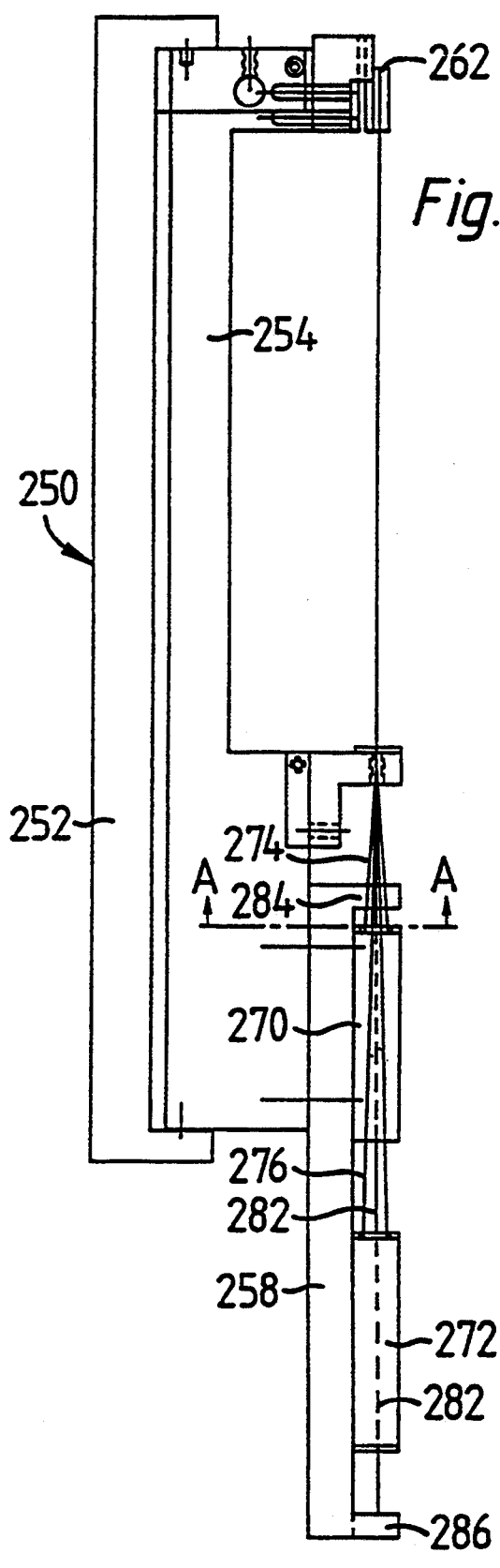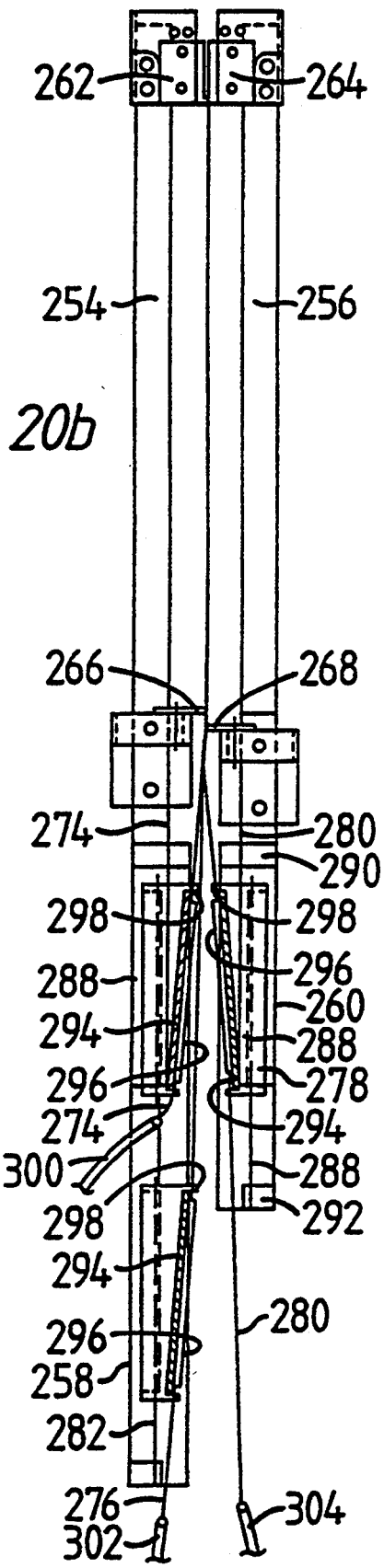
Fig. 20a
Fig. 20b

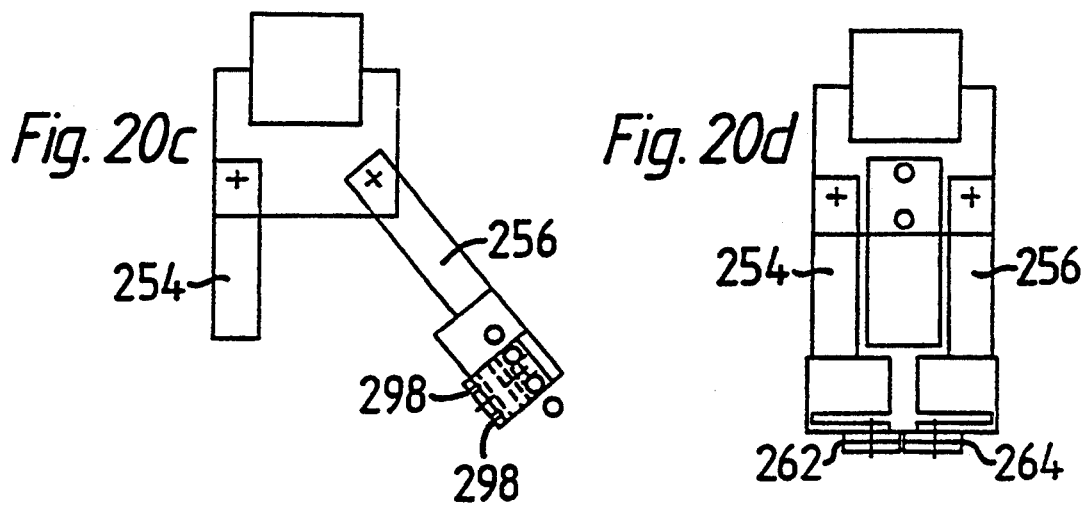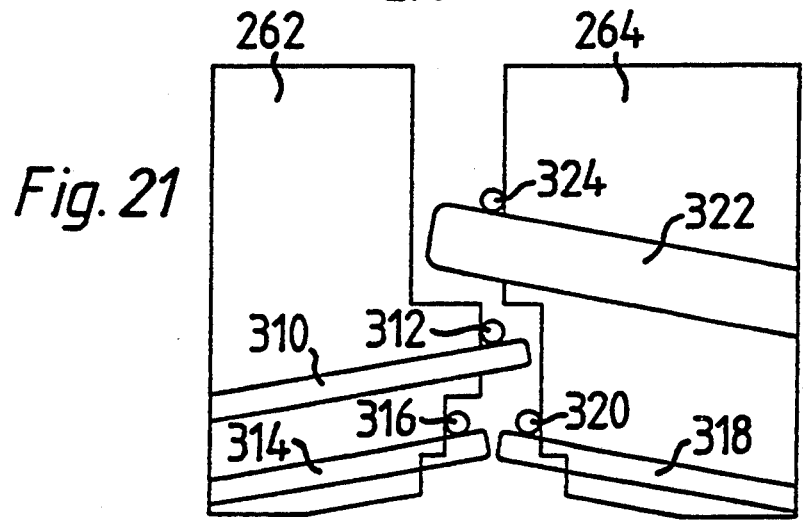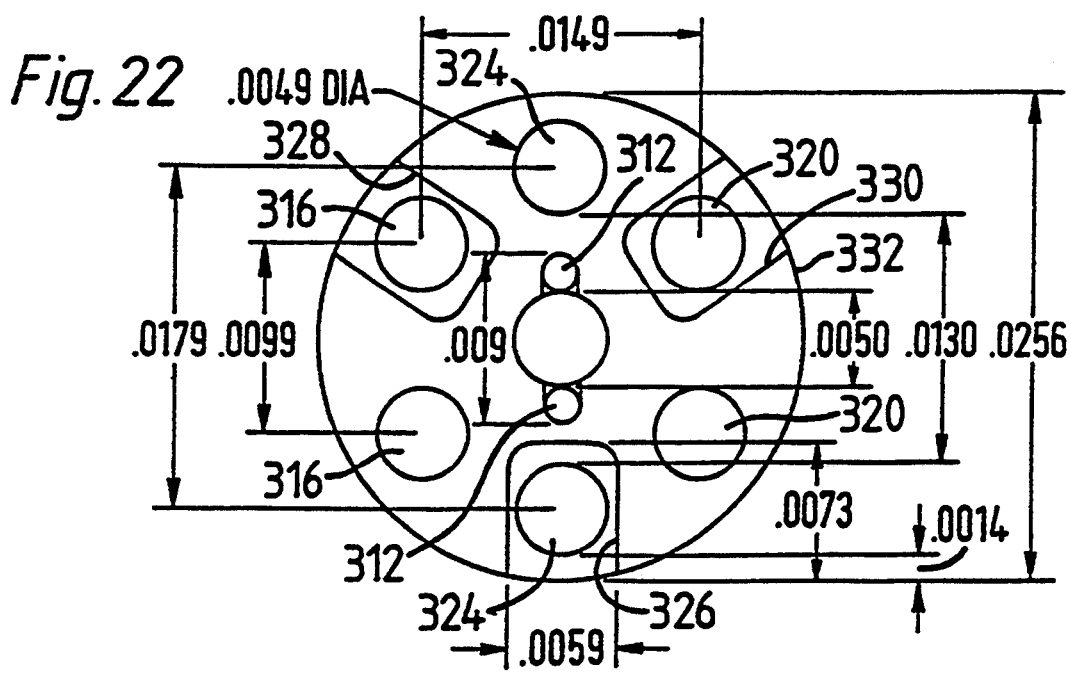

OPTICAL SENSOR FOR FLUID PARAMETERS

RELATED APPLICATIONS

This application is a continuation-in-part of U.S. application Ser. No. 07/810,479 filed on Dec. 19, 1991 now allowed which is itself a division of U.S. Pat. No. 5,124,130.

BACKGROUND OF THE INVENTION

1. Field of the Invention

This invention is directed to methods and apparatuses for making optical sensors and to optical sensors. In one specific aspect, this invention is directed to multi-fiber fiber optic sensors and to methods for making them. In one specific aspect, this invention is directed to multi-fiber fiber optic sensor probes for sensing blood gas levels in vivo. In another aspect multiple sensors are used in one catheter-like probe.

2. Background of the Invention

In 1985, David Costello, one of the co-inventors named in this application, filed his application entitled "Fiber Optic Probe For Quantification of colorimetric Reactions" which resulted in the issuance of U.S. Pat. No. 4,682,895. This patent claims an optical sensor for the colorimetric measurement of chemical properties which can be inserted into living tissue, e.g. into the blood vessels of a human being. This optical probe allows arterial blood gases to be monitored within a patient with a fiber optic sensor placed through an arterial cannula or arterial line, whereas before values for such gases were measured in a laboratory in blood samples taken from the patient.

With the new sensor, real-time determination of a biochemical parameter or blood gas value is possible, providing up-to-the minute information to a physician. This can be of critical importance with an unstable patient whose biochemical parameters and blood gases may change dramatically over a short period of time. Real-time current and trend information is much more valuable to a physician than the previously-available discrete historical data.

In addition to the unique fiber optic probe of U.S. Pat. No. 4,682,895, other fiber optic sensor designs are available. One such design uses a reflection-based optical path (Peterson & Goldstein) In another design a fluormetric indicator system is employed (Vurek; Munkolm & Watt; Lubbers). Devices incorporating these designs have been made using extrusion/insertion techniques or co-extrusion techniques. Incorporated fully herein by reference is "Chemical Sensors Based On Immobilized Indicators And Fiber Optics," by W. Rudolf Seitz from CRC Critical Reviews in Analytical Chemistry, Vol. 19, Issue 2, 1988 which describes various prior art fiber optic sensors.

There has long been a need for a reliable and efficient process for the production of fiber optic sensors and multi-sensor probes. There has long been a need for a multiple sensor device and efficient and reliable methods for its production. There has long been a need for an automated process for producing multi-fiber optic sensors. There has long been a need for such a probe which can be easily introduced into small tubes, e.g. blood vessels. There has long been a need for a fiber optic sensor in which multiple optical fibers have a precise arrangement, and a need for a process for making such sensors.

SUMMARY OF THE PRESENT INVENTION

The present invention provides fiber optic sensors and methods for their fabrication. In one embodiment of the present invention a manufacturing process is provided in which one or more optical fibers are looped over one or more small diameter mandrels or spokes of a suspension spider. The mandrels are arranged in a radially symmetrical pattern so that they intersect at a single point. Tension is applied along the length of the fibers to form bends at their midpoints. By controlling the amount of tension, a bend of a desired radius can be produced. In a preferred embodiment, the radius of the bend, measured from the center of the bend to the central axis of the fiber, will be approximately the sum of the radii of one mandrel and that of one fiber. By using mandrels with a diameter equal to that of a fiber, the resulting bends in one embodiment will have a radius approximately equal to the diameter of the optic fibers. A tip support coating can be applied to the fibers in the region near the bend to cement the fibers in place. After it hardens the mandrels are removed. An optical gap which provides a site for a photometric reaction is made in the fiber, e.g. by cutting out a portion of the fiber or by using a laser to ablate a gap. The gap may be located as desired. In one embodiment the gap is located away from the bend along the length of the fiber.

An apparatus for making multi-channel sensors according to the present invention, in one embodiment has a holding jig or spider with an open center and holes spaced around the center. Mandrels or spokes (e.g. of wire, thread, suture, or of fiber optic material) are threaded through pairs of holes to intersect at an open center area and divide the open center area into wedges. The ends of the optic fibers are inserted into the wedges, preferably one per wedge. The fiber ends are clamped to a fabrication stand which is flexible so that, by bending the stand and readjusting the clamp, varying degrees of tension are applied along the optic fibers. A tip support coating, e.g. epoxy cement or other encapsulant is applied to the tip of the fiber bundle in the area of the mandrels and extending down the fiber bundle. This insures that the fiber geometry and disposition will be maintained. After the epoxy has cured the mandrels are removed by cutting them off close to the intersecting point. In another embodiment the mandrels are lubricated so they will slide away from the fibers.

Under microscopic examination it has been observed that in one embodiment one half of each fiber can be made to tend toward the outside edge of the completed probe by proper placement of the fibers. This gives the probe in this embodiment a rounded triangular cross section and facilitates removing a slice from each fiber, e.g. with a diamond edged wafering saw. In another embodiment the use of cantilevered micro hooks for fiber suspension permits a more-rounded probe shape.

During curing of encapsulant or potting material a heat shield can be placed over the point of fiber intersection to keep the fibers from being damaged by heat applied during the curing process. The fiber optic bundle thus arranged may be exposed to conditions required for curing the encapsulant material. If the material requires elevated temperature the fabrication stand may be located within or moved into an oven. In a preferred embodiment the encapsulant may be cured by exposure to ultraviolet light, thus, the fabrication stand is located in a cabinet with a high intensity light source fixed so as to irradiate the fibers when the light is switched on.

Before or after treatment of the fibers, a desired material can be applied to the fiber and to the tips of the fiber. Various biologically compatible materials, e.g. but not limited to silicones and siloxane coatings can be used so that the sensor is implantable in living tissue.

Tension may be applied to the fibers in a variety of ways, including but not limited to: stretching the fibers and clamping them in place; fixing the mandrels in place on a frame and weighting the fiber ends; or applying magnetic force to ferromagnetic elements applied to fiber tips or mandrels. Tension can also be applied by having a vacuum chuck receive and hold the fiber ends distal from the fiber bend.

In one embodiment of the present invention the multi-sensor probe is inserted into a protective sheathing or harness and then each individual optical fiber is provided with appropriate fiber optic connectors. A protective housing can be provided around the harness to protect the probe device until it is used. By appropriate connection of the probe device to a sensor interface unit and a base unit, real time data from the sensor can be made available.

The optical gaps or chambers formed in the optical fibers can be filled with a desired chemical indicator, e.g. phenol red, phenolphthalein, or perylene dibutyrate. Indicators may be immobilized by chemically binding them to the surface of solid particles, e.g. porous glass particles, latex microspheres, or adsorbent polymers such as styrene or polydivinyl benzene. These solid particles may be held in place within the optical gap by a gel e.g. a solution of hydroxy propyl-cellulose. A selectively permeable membrane is applied over the indicator containing gap to prevent loss of the indicator compound or contamination by undesired chemical species in the environment.

In another embodiment of a process according to the present invention, fibers are emplaced over cantilevered micro hooks disposed above magnetic positioning clamps secured to weights which provide tension to hold the fiber bends in place on the cantilevered micro hooks. To facilitate and simplify the process, the free fiber ends are received in and held in small diameter tubes to which a vacuum has been applied. The cantilevered micro hooks are disposed on pivotable arms for ease of disposition. After one or more fibers have been positioned on the arms, the arms are moved together so that the fibers, and particularly the fiber bends are disposed with respect to each other as they will be in the finished probe. Thus, a more-rounded configuration of multiple fibers can be achieved, rather than triangular, which occupies less total space. In this embodiment during the fabrication process the fibers hang independently of each other and each fiber has its own applied weight for tension and its own set of vacuum tubes. Thus the fibers do not compete for disposition on a mandrel or push against or down on each other. By applying heat to the fiber bends while the fibers hang on the cantilevered micro hooks while temporarily increasing the tension on the fibers by adding more weight to the fibers (e.g. doubling the weight) internal stresses in the fibers are relieved and the tendency of the bends to pop back is reduced, insuring that the desired bend will be maintained. Potting encapsulant material is then applied to the fiber bundle. Curing of certain preferred potting materials is accomplished by subjecting them to ultraviolet radiation. Intermittent application of the beam is desired to give the fibers a rest between curing pulses and to protect them from melting and heat damage. After the fibers are removed from the cantilevered hooks and vacuum tubes, the bends are also potted (in addition to several inches of the fibers that are potted prior to removal from the hooks). The potted tip is then subjected to the u.v. lamp beam for curing.

It is, therefore, an object of the present invention to provide new, unique, useful, efficient, effective and non obvious fiber optic sensors and probes and methods for making them.

Another object of the present invention is the provision of apparatuses useful in such methods.

A further object of the present invention is the provision of such methods wherein a bend can be provided in an optical fiber, the bend having a desired useful radius.

Yet another object of the present invention is the provision of such methods in which various encapsulant or potting materials are effectively applied to bent fibers and cured without adverse heat effects and so that fibers do not adhere to each other and are kept separate from each other.

Another object of the present invention is the provision of such sensors in which an optical gap is provided in optical fibers by cutting out a portion of the fiber or by removing a portion of the fiber with a laser.

An additional object of the present invention is the provision of such methods that include processes for inserting chemical indicators into optical gaps or chambers in optical fibers; immobilizing such indicators; and applying a semi-permeable membrane on such indicators.

A further object of the present invention is the provision of apparatus for producing such sensors, including a mandrel device for holding and separating a plurality of optical fibers and apparatus for providing tension to such fibers to produce a desired bend on the fibers and to immobilize the fibers during curing of materials applied to the fibers.

Another object of the present invention is the provision of a fiber optic sensor and probes with such sensors in which a bend in the optical fiber(s) has internal stresses relieved by a heat treatment.

Yet another object of the present invention is the provision of a method for producing a fiber optic probe with multiple optical fibers in which the fibers are disposed independently of each other during the fabrication process.

A further object of the present invention is the provision of a vacuum chuck for holding ends of optical fibers.

Other objects of at least certain preferred embodiments of the present invention include the provision of: sensor probes with opaque coatings over portions thereof for enhancing signal transmission and reducing outside effects on such signals, and methods for applying such coatings; new automatic potting methods; chemical indicator installation methods and methods for applying films, coatings, and membranes over them; methods for installing a thermocouple in a device; methods for making a probe or sensor and such probes or sensors; and methods for applying an anti-thrombogenic material to a probe or sensor and to associated devices.

The present invention recognizes and addresses the previously-mentioned long-felt needs and provides a satisfactory meeting of those needs in its various possible embodiments. To one of skill in this art who has the benefits of this invention's teachings and disclosures, other and further objects and advantages will be clear, as well as others inherent therein, from the following description of presently-preferred embodiments, given for the purpose of disclosure, when taken in conjunction with the accompanying drawings. Although these descriptions are detailed to insure adequacy and aid understanding, this is not intended to prejudice that purpose of a patent which is to claim an invention no matter how others may later disguise it by variations in form or additions of further improvements.

DESCRIPTION OF THE DRAWINGS

So that the manner in which the above-recited features, advantages and objects of the invention, as well as others which will become clear, are attained and can be understood in detail, more particular description of the invention briefly summarized above may be had by reference to certain embodiments thereof which are illustrated in the appended drawings, which drawings form a part of this specification. It is to be noted, however, that the appended drawings illustrate preferred embodiments of the invention and are therefore not to be considered limiting of its scope, for the invention may admit to other equally effective equivalent embodiments.

FIG. 1 is a cross-sectional view of an optical fiber in tension around a mandrel according to the present invention.

FIG. 2 is a top view of the fiber of FIG. 1

FIG. 3a is a side view of a plurality of optical fibers on mandrels according to the present invention. FIG. 3b is a top view of the fibers of FIG. 3a.

FIG. 4a is a side view of a plurality of optical fibers on mandrels according to the present invention. FIG. 4b is a top view of the fibers of FIG. 4a.

FIG. 5a is a side view of a plurality of optical fibers on mandrels according to the present invention.

FIG. 5b is a top view of the fibers of FIG. 5a.

FIG. 6 is a side view of an apparatus used in methods for fabricating an optical probe according to the present invention.

FIG. 7 is cross-sectional view of a vacuum chuck as used in the apparatus of FIG. 6a.

FIG. 8a is a top view of a "spider" according to the present invention. FIG. 8b is a side view of the spider of FIG. 7a.

FIG. 12 is a cross-sectional view of an optical chamber according to the present invention.

FIG. 13 is a cross sectional view of an optical chamber according to the present invention.

FIG. 14 is a cross sectional view of an optical chamber according to the present invention.

FIG. 15 is a side view of a probe according to the present invention.

FIG. 16 is a schematic view of a probe system according to the present invention.

FIG. 17 is a side view in cross-section of a protective housing for part of a probe according to the present invention.

FIG. 18 is a side view of the probe in FIG. 15.

FIG. 19 is a side view of the tip of the probe in FIG. 15 and part of the intra-arterial cannula of FIG. 15.

FIG. 20a is a side view of an apparatus for producing probes according to the present invention. FIG. 20b is a front view of the apparatus of FIG. 20a. FIGS. 20c is a view along line A-A of the apparatus of FIG. 20a. FIG. 20d is a top view of the apparatus of FIG. 20a.

FIG. 21 is a detailed side view of fiber holders of the apparatus of FIG. 20a.

FIG. 22 is a cross-sectional view of a probe made as shown in FIGS. 21 and 20a.

FIG. 27 is a partial top view of a fiber guide of the apparatus of FIG. 20a.

FIG. 28 is a partial top view of a fiber guide of the apparatus of FIG. 20a.

FIGS. 33–36 are side cross-sectional views of sample or indicator containing chambers of the probe of FIG. 30a.

DESCRIPTION OF PREFERRED EMBODIMENTS

Figure 9:
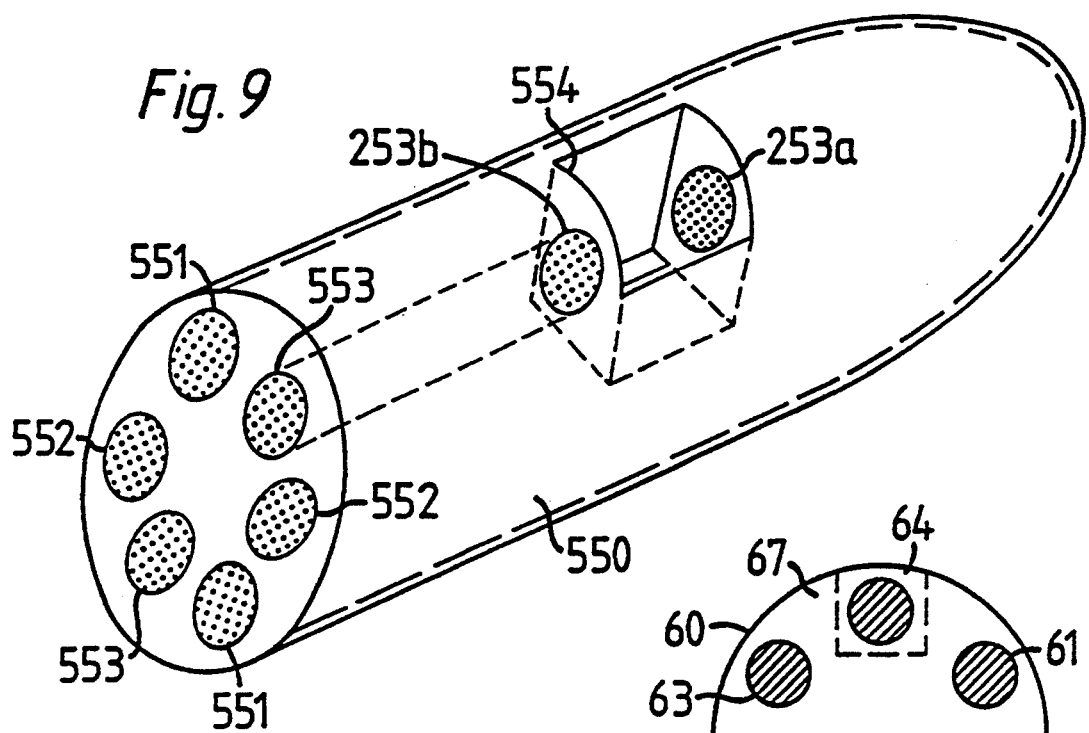
FIG. 9 is a perspective view of a bundle of optical fibers showing an optical chamber according to the present invention.

Referring now to FIGS. 1 and 2, an optical fiber 10 of diameter "a" is shown in tension around a mandrel 12, producing a bend 14 in the fiber. A radius of the bend 14 is approximately equal to the diameter a of the optical fiber 10. The particular geometry and configuration of the optical fiber 10 is maintained by applying a tip support coating (also referred to as an encapsulant or potting material) 18 around the fiber 10. After the tip support coating 18 has been applied and cured, the mandrel 12 may be removed by cutting it close to the fiber optic bundle and carefully withdrawing it. Another layer of coating can be applied to the fiber by dipping or spraying on the appropriate material to seal the hole left by the mandrel.

An optical gap 20 (also referred to as a "sample chamber") is provided in the fiber 10 for containing and holding a chemical-indicating colorimetric material. Methods for creating such gaps will be discussed below.

As shown in FIGS. 3a and 3b, a common radial configuration may be employed for multiple optical fibers. Three optical fibers 30, 31, 32 are stacked on top of a three-mandrel stack of mandrels 33, 34 and 35. In this configuration the fibers contact each other and compete for position on the mandrels. Half of each fiber resides slightly recessed within the total cross-section of multi-fiber arrangement. Each fiber is thus disposed so that it is presented for convenient and effective formation of an optical gap sample chamber.

As shown in FIGS. 4a and 4b, mandrels 43, 44, and 45 are stacked with a common radial pattern as viewed from above (FIG. 4b) but the mandrels are spaced apart by optical fibers 40, 41, and 42 disposed on the mandrels. In this configuration the optical fibers do not bear down directly on each other, particularly where tension is applied.

A three channel probe was made of the configuration of FIG. 3a using plastic fiber and wire mandrells with 250 micron diameters. The resulting probe had a maximum diameter of 1.56 mm. Three probes were made with optical fiber mandrells and optic fibers with 125 micron diameters. These probes had maximum diameters of 630 microns, 800 microns, and 584 microns. The maximum diameter of the finished probe is inversely related to the tension applied to the fiber bundle during fabrication.

Referring now to FIGS. 5a and 5b, optical fibers 50 and 51 are supported by a mandrel 53 and a mandrel 54 supports an optical fiber 52 spaced apart from the fibers 50, 51 and the mandrel 53. The mandrels 53 and 54 may be spaced apart any desired and workable distance. The fibers 50, 51, and 52 may have different bend radiuses. These radiuses may be varied to produce an arrangement that is of a desired overall shape, e.g. circular or rectangular. These different shapes of the fiber bundle facilitate cutting of the optical gap or they enhance the flow profile of fluids flowing past the sensor in use.

As shown in FIGS. 5a and 5b, the optical fibers may be positioned so that they are not in contact with each other. This provides complete separation of sensor channels and facilitates positioning and removal of mandrels. It is, however, within the scope of this invention to provide such an arrangement in which a fiber does contact an adjacent fiber.

With respect to the arrangement shown in FIGS. 3a, 4a, and 5a, three fibers are shown. It is within the scope of this invention to employ two or more fibers in such arrangements. Of course using a greater number of fibers will increase the overall size of the resulting multi-fiber sensor.

Referring now to FIG. 6 an apparatus 150 according to the present invention has an upright member 152 to which are secured a top spider 154, a mid-position spider 156 and a vacuum chuck 158. These items may be semipermanently secured to the upright member 152 so that they can be moved and positioned as desired. The upright member 152 is secured to a top arm 160 and a bottom arm 162 which in turn are pivotally connected to a wall 164 by pivots 166 and 168 respectively. The wall 164 is mounted on a base 174. Radiation from an ultraviolet lamp 170 passes through a quartz window 172 in the wall 164 to cure potting encapsulating material applied to a bundle 176 of one or more fibers disposed between the spiders 154, 156 and the vacuum chuck 158. The vacuum chuck is movably disposed on the upright member 152 to facilitate the handling of ends of the fibers in the bundle 176 and to provide adjustability of the tension on the fibers. A shield 178 movably connected to the wall 164 can be moved into position to shield personnel from radiation emitted by the lamp 170. An electrostatic charge neutralizer 180 secured to the wall 164 eliminates electrostatic charges in the fibers.

Pulsed intermittent application of the radiation from the u.v. lamp 170 can be achieved by alternately turning the lamp on and off or by periodically blocking the beam. As shown in FIG. 6, a shutter 171 is disposed so that it may be moved to close off the quartz window 172. The shutter 171 is shown as connected to a motor 173 which operates to move the shutter 171 toward and away from the quartz window to achieve the desired pulsing of radiation for curing fibers. Pulses of 0.75 seconds duration are preferred for preferred potting materials; pulses of longer duration might cause a damaging temperature rise in the fibers. A heat shield can be placed over the fiber bends on the spider during this curing operation to protect them from heat damage.

Referring now to FIG. 7, a vacuum chuck 194 (like the vacuum chuck 158 of FIG. 6) has a chuck body 196 with a chuck funnel 198 having a concave funnel opening 200 for receiving fiber ends and a funnel bore 202 through which the fiber ends pass into a funnel chamber 204. The chuck body 196 is movably mounted above a dash pot 206 and comes to rest on a top member 208 of the dash pot 206 which is mounted on a dash pot base 210. When the chuck body 196 moves downwardly, a ram 212 moves into a bottom bore 214 of the funnel bore 202, clamping the fiber ends between the ram and an O-ring 218 in the funnel bore. The rod is sealed by a bottom seal 216. A vacuum is applied to the chuck by a vacuum pump 217 (FIG. 6) through an opening 219. The vacuum chuck applies minimal tension to the fibers.

As shown in FIGS. 8a and 8b, a spider disc 182 (used e.g. with the spiders 154 and 156 of the apparatus 150) has six slots 184 and six notches 186 in a middle ridge 188 surrounding a hole 190. Wires 192 passed through these notches and slots and secured to the disc serve to separate optical fibers held therebetween. Dimensions indicated are in inches.

Referring now to FIG. 9, a probe 550 according to the present invention with coatings and membranes as previously described (and like the probe 60 described below) is shown containing three optical fibers 551, 552, 553. An optical gap sample chamber 554 is shown as a five-walled chamber. The gap is about 100 microns long and can be, preferably, 85 to 115 microns long. Preferable gap depth ranges between 130 and 160 microns. The probe 550 is about 700 microns in diameter. It is preferred that this chamber be formed by using an excimer laser because use of such a laser provides precise location, exact dimensions, and an optically clear finish to cut fiber faces 253a and 253b.

Figure 10:
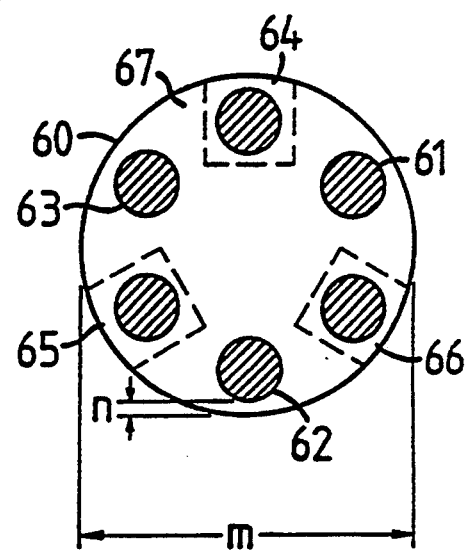
FIG. 10 is a cross-sectional view of a bundle of optical fibers according to the present invention.
Figure 11A:
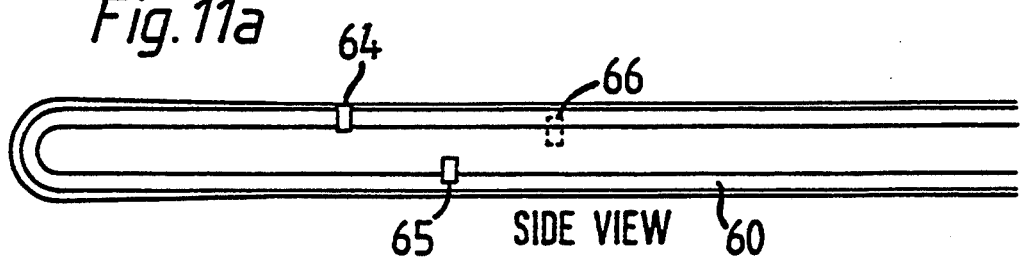
FIG. 11a is a side view of the probe of FIG. 10.
Figure 11B:
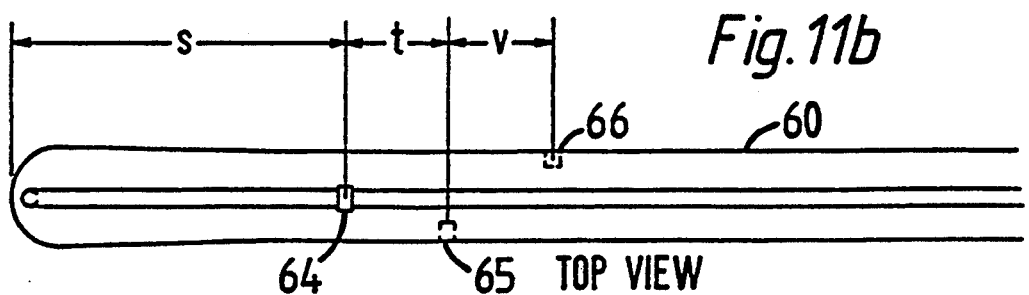
FIG. 11b is a top view of this probe.

As shown in FIGS. 10, 11a and 11b, a probe 60 according to the present invention has three optical fibers 61, 62, and 63 encapsulated in cured potting material 67. Each fiber 61, 62, 63 is associated with a sample chamber 64, 65, 66, respectively. The distance m is the outside diameter of the fiber optic probe 60 and should be controlled as appropriate for the intended use of the probe. As an example, if the intended use is for insertion through an arterial cannula the outside diameter should be small enough to fit easily through the cannula. The distance n is the thickness of encapsulant material lying over a particular fiber. This distance affects the volume of the sample chamber, the separation of the light path from the outside environment, and the outside diameter of the probe. The probe 60 has been coated (undercoating, overcoating, e.g. as in FIG. 12) and the chambers 64, 65, 66 are like the chambers 70, 80, 90, respectively (FIGS. 12, 13, 14). Membranes have been applied over the chambers 64, 65, 66 as for the chambers 70, 80, 90.

In the embodiment of FIGS. 10, 11a, and 11b, the longitudinal distance s from chamber 64 to the tip end of the probe is about 2540 microns and preferably is in the range of 2240 to 2840 microns. The distance longitudinal t between chambers 64 and 65 is 790 microns and is preferably in the range of 915 to 665 microns as is the distance v between the chambers 65 and 66. This preferred longitudinal spacing minimizes the depth of intrusion into, e.g. a human blood vessel, yet reduces structural weakness which might be caused by chambers spaced closely together. This spacing also facilitates loading of chemical indicators into gaps as well as the application of membrane material over gaps.

A pH sample chamber 70 through an optical fiber probe 79 according to the present invention is shown in FIG. 12. The chamber 70 has an undercoating 72 (preferably of a water impermeable polymer such as commercially available Petrarch SE, Teflon, or Perylene), to protect the sample chamber from changes in chemical concentration due to the diffusion of water and an overcoating 74 of the same material. The undercoating 72 may be of multiple layers to increase resistance to water transport; a pH indicating material 76 (e.g. phenyl red, buomocresol green, or other subtalein indicators that react, e.g. change color or fluoresce upon a change in pH) and a selective membrane 78 (e.g. nitro cellulose or porous hydrophilic polymers). The membrane selectively permits hydronium ions to flow from outside the probe 79 into the sample chamber 70. The coatings are applied before gaps are formed.

As shown in FIG. 13, a carbon dioxide sample chamber 80 according to the present invention through an optical fiber 89 has an undercoating 82 (like 72); an overcoating 84 (like 74); a $CO_2$ indicator 86 (e.g. phynol red combined with bicarbonate or other pH indicator); and a selective membrane 88 which selectively permits $CO_2$ to pass from outside the fiber 89 into the sample chamber 80. The $CO_2$ reacts with water present in the sample chamber to create carbonic acid which in turn reacts to change the color of the pH indicator present in the chamber. Essentially any pH indicator may be used to indicate CO by combining the indicator with bicarbonate and isolating the reaction from hydronium ions in the environment while permitting access to $CO_2$.

Referring now to FIG. 14, an oxygen sample chamber 90 through an optical fiber 99 has: an undercoating 92; an overcoating 94; and oxygen-indicating colorimetric substance 96 [(e.g. BASF Fluorol Green Gold (perylene di-butyrate)] or other fluorescent chemicals with fluorescent lifetimes such that they are quenched in response to the presence of oxygen; and an oxygen semi-permeable membrane 98 (e.g. silicone rubber or Teflon (TM) material, PTFE, porous polypropylene or porous polycarbonate) which selectively permits oxygen to pass from outside the fiber 99 to the oxygen-indicating substance 96.

With phenol red material immobilized on porous glass, the glass and membrane are supported by a material such as hydroxy propyl cellulose or hydroxy ethyl cellulose (plus bicarbonate for $CO_2$). An immobilizer is used to prevent phenyl red (indicator) from migrating out of the sample chamber. The support material can be applied manually by mixing it with porous glass. Cellulose acetate is applied to the entire tip of a sensor to separate the sample chamber from the exterior environment to insure only the desired analyte comes in and to hold the indicator in the sample chamber.

A measurement of $CO_2$ or oxygen concentration accomplished by the probe of FIG. 14 can be expressed as a partial pressure of total gas.

As shown in FIG. 18 a probe 100 (like the probe 60) according to the present invention has a bundle of optical fibers 232 which extend through a connector 232. As shown in FIG. 17 the probe's bundle of fibers is glued into a male luer 234 with adhesive 235. (Bundle 232 is like previously described bundle 60.) The connector 230 is made preferably from poly carbonate plastic. As shown in FIG. 17, a protective tube 242, preferably made from polyvinylchloride tubing is secured around the male luer 234 and provides strain relief. The fiber bundle 232 is surrounded by a black inner tube 238, preferably made from polyethylene to provide lubricity in the interior of the tubing to facilitate the passing of fibers therethrough; the black color prevents ambient light from affecting the fibers. A protective tube 240 surrounds the tube 238. The tube 240 is made preferably from polyethylene and extends from the connector 230 to a junction box 231 (FIG. 16). The tube 242 surrounds a portion of the tube 240, as does a tube 244 (like tube 242) adjacent the junction box 231. In one embodiment the distance from the male luer 234 to the junction box is about 12 inches. As shown in FIG. 15 the probe 100 has been disposed in an intra-arterial cannula 101. As shown in FIG. 16, the probe 100 may then be connected to a sensor interface unit 120 (shown as separate from a base unit but which could be incorporated therein) which is connected to a base unit 122. The sensor interface unit provides light input to the probe and detects and measures light coming out of the probe. Signals from the unit 120 are then fed into the base unit where they are processed for display or recordation or both.

As shown in FIG. 19, a tip 103 of the probe 100 extends into the intra-arterial cannula 101. The cannula 101 is suitable for introduction into and disposition within a human blood vessel. The tip 103 is disposable in the cannula (e.g. when the cannula is emplaced in an artery) by connecting the luer y connector 102 to the cannula and then inserting the probe 100 into the cannula through one channel 107 of the luer y connector. It is preferred that the distance k from the end of the cannula to the tip of the probe be such that there is good "washability" or fluid flow over the sample chambers; e.g. in certain preferred embodiments this is about 4910 microns. It is preferred that the distance from the end of the cannula to the first adjacent sample chamber be such that fluid injected through the luer y connector does not diffuse into the blood in the region of the sample chambers producing erroneous readings; e.g. in preferred embodiments this is about 790 microns. Whatever fluid was being introduced into or withdrawn from the cannula may be introduced or withdrawn from a channel 105 of the luer y connector through which the probe 100 does not extend.

FIGS. 20a–20d illustrate another apparatus 250 for fabricating a multi-fiber probe according to the present invention. The apparatus 250 has an upright member 252 to which are pivotably connected two arms 254 and 256. A weight holder 258 is secured to the arm 254 and a weight holder 260 is secured to the arm 256. A micro pin mount 262 is secured to the top of arm 254 and a micro pin mount 264 is secured to the top of the arm 256.

Figure 26:
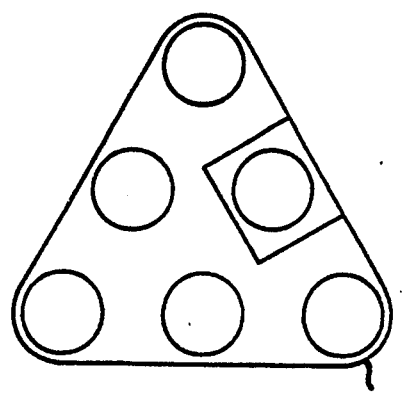
FIG. 26 is a cross-sectional view of two probes according to the present invention.
Figure 27:
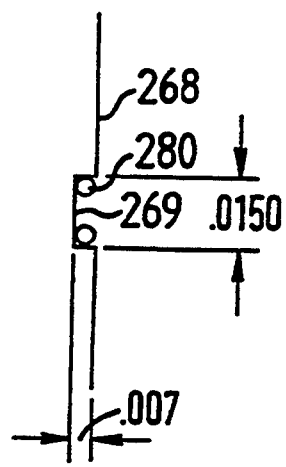
Figure 28:
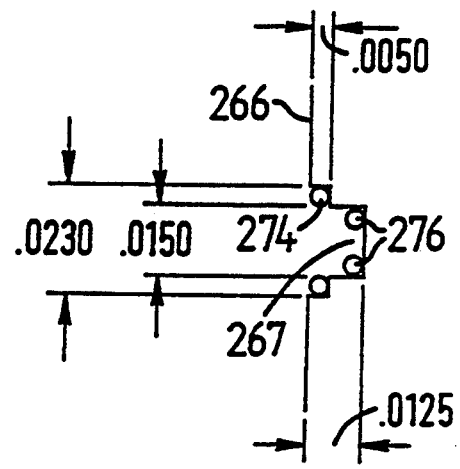

A fiber guide 266 is secured to a bottom portion of the arm 254 and a fiber guide 268 is secured to a bottom portion of the arm 256. The micro pin mount 262 has two micro pins, each for independently holding an optical fiber. The weight holder 258 has two weights, 270 and 272, one each for each of two fibers 274 and 276 supported from the micro pin mount 262. The weight holder 260 has a weight 278 for a fiber 280 supported from the micro pin mount 264. The weights 270, 272 and 278 are freely movable up and down on a wire extending through the weights; wire 282 extending through weights 270, 272 and secured to a top arm 284 and a bottom arm 286 of the weight holder 258; and wire 288 extending through the weight 278 and secured to a top arm 290 and a bottom arm 292 of the weight holder 260. Each weight has a sheet magnet 294 secured thereto. Fibers are clamped between the fixed magnets 294 and a free sheet magnet 296 which provides a sufficient clamping effect to hold the fibers and hang the weights from them to provide the desired tension. Each weight weighs about 18 grams. Notches are provided in the fiber guides 266, 268 and in a top shoulder 298 (e.g. FIG. 20c) of each weight so that the fibers are held separately and independently in the apparatus 250. As shown in FIG. 27 the fiber guide 268 (shown partially) has a recess 269 for receiving and holding the fiber ends of the fiber 280. The fiber guide 266 (shown partially in FIG. 28) has a recess 267 for receiving and holding the fiber ends of fibers 274 and 276. (Dimensions in FIGS. 26, 27 are in inches) This insures formation of a probe of desired configuration. Three pairs of vacuum tubes 300, 302, 304 receive and hold the ends of each of the fibers 274, 276, and 280 respectively. Each tube receives and holds one fiber end. By thus holding the fiber ends, the use of the apparatus and handling of the fibers is facilitated and some minimal tension is applied to the fibers.

Since the arms 254 and 256 are pivotable with respect to the upright member 252 one or more fibers can easily be emplaced on each arm's micro hooks prior to closing of the arms. Closing the arms into proximity with each other moves the fibers into a desired relationship with each other so that an ultimate configuration and size for a multi-fiber probe is achieved.

Potting encapsulant material (e.g. commercially available ELC 4481 of Electro-Lite Corp.) can be applied manually to the exposed portion of the fibers between the top portions and bottom portions of the arms 254 and 256.

As with the apparatus 150 a lamp may be used with the apparatus 250 for curing the potting encapsulant material.

Internal stresses in the fiber bends around the micro hooks can be relieved by applying heat to the micro hook holders, the micro hooks, and the fiber bends while the fibers are still emplaced on the apparatus 250 before the application of potting material. For example, hot air at about 80° C. is blown at the micro hook holders. The holders and hooks heat up gradually (e.g. in about 90 seconds) so that the temperature of the fiber bends comes up to about 80° C. This helps to make the bends more permanent and reduces the tendency of the fibers to spring back. Auxiliary weights (e.g. double the weight of the weights 270, 272, 278) are temporarily applied to the fibers (e.g. by hanging onto the weights 270, 272, and 278) during the heat treatment to achieve optimum bending stress while the temperature is elevated.

The potted cured fibers are removed from the apparatus. Potting material is applied to the tip of the assembly—the portions hanging over the micro hooks including the fiber bends. This material is cured. Thus the fiber bends and a portion of the fibers adjacent the fiber bends is covered with cured potting material and the fibers (and thermocouple or other device) in these portions are not in contact. The harness (tubing, connector, junction box) is assembled and then gaps are formed in the fibers. coatings are applied; indicators are emplaced in the gaps; and membranes are applied over the gaps by placing membrane material dissolved in a suitable solvent over the gaps (sample chambers); e.g. cellulose acetate in acetone as a membrane over a pH indicator, polydimethyl siloxane in methylene chloride as a membrane over a $CO_2$ or $O_2$ chamber or polycarbonate in chloroform. The resulting assembly is a multi-fiber device useful in an optical sensor probe.

FIG. 21 shows the fiber holders 266, 268 in more detail. These holders are configured so that the fibers to be worked with and treated hang independently of each other. Fiber holder 266 has a cantilevered pin 310 from which hangs a thermocouple 312 [not shown in FIGS. 20a, b] and a cantilever pin 314 from which hangs a fiber 316. The pins are preferably disposed at an angle to maintain the fibers thereon. Fiber holder 268 has a cantilevered pin 318 from which hangs a fiber 320 and cantilevered pin 322 from which hangs a fiber 324. The pins 310, 314 and 318 are emplaced in grooves that are about 5 mils wide. The pin 322 is emplaced in a groove that is about 13 mils wide. Thus a fiber hanging over pin 322 hangs with its ends spaced further apart than the ends of a fiber hanging over one of the other pins.

Figure 23:
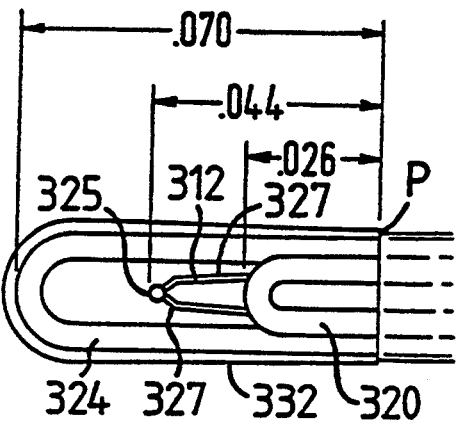
FIG. 23 is side view of the probe of FIG. 22.
Figure 24:
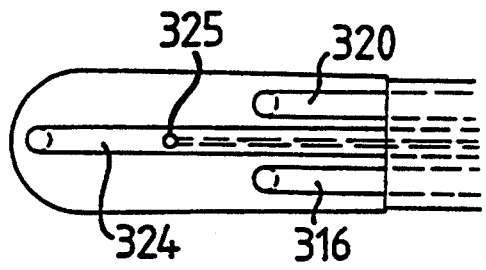
FIG. 24 is side view of the probe of FIG. 22.

FIGS. 22, 23 and 24 show a probe 332 (like the probe 60 previously described regarding sample chambers, coatings, and membranes) corresponding to the fabrication layout of FIG. 21. Dimensions given in FIGS. 22 and 23 are in inches. The distance between the strands of the thermocouple fiber is 0.005 inches. The size of sample chambers 326, 328 and 330 may preferably range in width between about 130 to about 160 microns with 145 microns preferred. The overall diameter of the probe 332 as shown is 650 microns (0.0256 inches) this diameter preferably ranges from about 600 microns to about 730 microns with preferred diameter being 650 microns. As shown there is a 0.0014 inches thick cured potting layer between the fibers and the exterior surface of the probe so it will fit easily through a 20 gauge cannula and permit blood to be withdrawn therefrom. This also separates the membrane from the optical path. As shown in FIGS. 22 and 24 the fibers 316, 320, and 324 and thermocouple 312 do not contact each other in the tip end of the probe. The thermocouple 312 has a small (e.g. 10 mil) metal bead 325 to which are connected two 2 mil diameter metal leads 327. Commercially available Type E thermocouples can be used or a thermister. As shown in FIG. 23 the length from line P (line P represents the extent of the potting material applied to the probe tip) to the exterior of the first fiber bends is about 0.026 inches. A preferable range for this distance is 0.020 to 0.031 inches. The distance from point P to the thermocouple is about 0.044 inches (and ranges preferably between 0.040 and 0.051 inches). The distance from point P to the end of fiber 324 is shown as about 0.070 inches (preferably ranging between 0.066 and 0.075 inches). The thermocouple is located preferably interiorly of all the fibers because it needs no tangentical access to fluids and it can occupy interior space not occupied by optical fibers.

Figure 25:
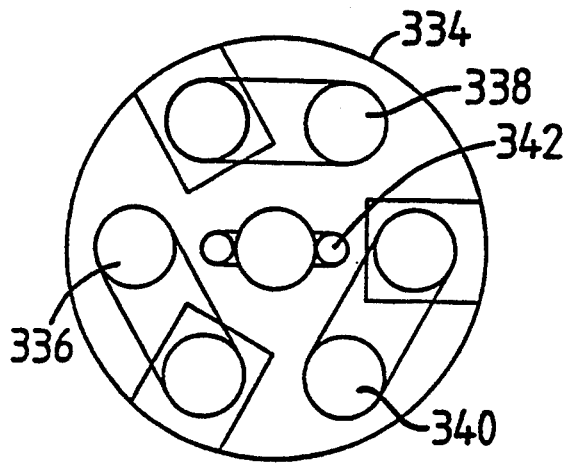
FIG. 25 is a cross-sectional view of a probe according to the present invention.

FIG. 25 illustrates a probe 334 in which all fiber bends (of fibers 336, 338 and 340) are of substantially the same diameter. A thermocouple 342 is present in the center of the probe 334.

FIG. 26 presents a fiber probe 346 produced with apparatus 150, 160 using a spider as shown in FIG. 4a. Since the fibers in the apparatus 150 contact and compete with each other for position, the generally triangular disposition achieved requires more potting encapsulant to effect a desired thickness of encapsulating material over the fibers. In this sense a circular configuration of the fibers of a probe (e.g. as shown in FIG. 10) is more efficient.

To summarize, one preferred method according to the present invention for forming an optical probe with a plurality (one or more) of optical fiber sensors includes the steps of: racking the fibers, i.e., emplacing them over hooks, a spider, or other suspension device producing bends in them; applying tension to the fibers, together or individually; applying potting material and curing it, in some embodiments first to the portion adjacent the bends and then to the bends themselves; introducing the fibers into a harness (connectors, tubing, junction boxes, etc.); forming gaps in the fibers; coating the fibers and gaps; introducing indicators into the gaps; and applying selective membranes over the gaps. Although certain preferred processes deal with bending a fiber and then cutting or ablating a gap, a gap can be formed by using two fibers, bending one, and positioning the second fiber near the first to form the gap.

In conclusion, therefore, it is seen that the present invention and the embodiments disclosed herein are well adapted to carry out the objectives and obtain the ends set forth at the outset. Certain changes can be made in the method and apparatus without departing from the spirit and the scope of this invention. It is realized that changes are possible and it is further intended that each element or step recited in any of the following claims is to be understood as referring to all equivalent elements or steps for accomplishing substantially the same results in substantially the same or equivalent manner. It is intended to cover the invention broadly in whatever form its principles may be utilized. The present invention is, therefore, well adapted to carry out the objects and obtain the ends and advantages mentioned, as well as others inherent therein.

Figure 29:
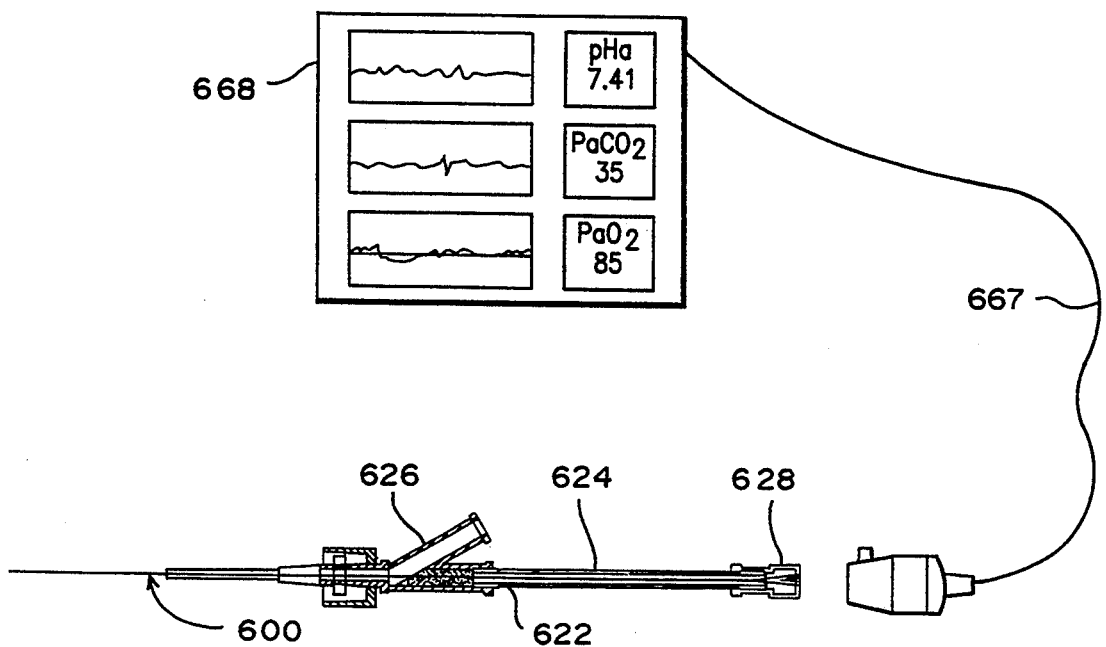
FIG. 29 is a schematic view of a system according to the present invention with a probe according to the present invention.

In another embodiment of the present invention, a probe 600 as shown in FIG. 29 is made by initially placing three optical fibers over three separate mandrels (micro hooks) of two different diameters, as described previously above, each fiber having a bent portion above its respective mandrel. Ends of each fiber are individually marked for ease of identification at a later stage of probe fabrication. A pull force is applied to the fiber ends to create a moderate tension in the individual strands to prevent overlap between the fibers and to maintain them in a parallel array. While the fibers are under tension and in place, heat is applied to the bend area to aid the formation of a uniform and precise bend of each fiber, which conforms to the mandrel's curvature and is made permanent by a thermoplastic set. The heat application assists in preserving the integrity of the core and cladding of the optical fiber. In one configuration, a thermocouple element is held on a separate mandrel within the bend area.

With the optical fibers and the electrically insulated thermocouple wires held taut in position, a UV (ultraviolet light) curable adhesive is uniformly applied to a short length of the taut fiber assembly proximal to the bend area. The application of such adhesive is done in a uniform vertical unidirectional manner. Intense and intermittent UV light is uniformly applied to the formed fiber assembly simultaneously and synchronously with the withdrawal of the adhesive applicator. The UV light applicators, preferably one on each side of the assembly, also move rapidly in a vertical unidirectional uniform manner along the longitudinal axis of the assembly.

Figure 30A:
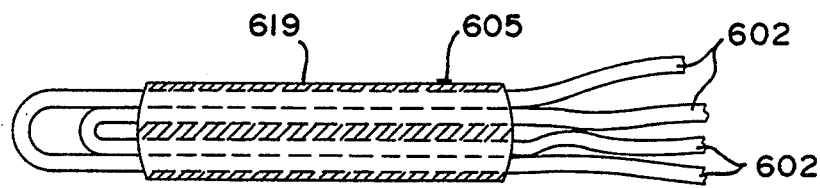
FIGS. 30a–30g are side cross-sectional views of part of the probe of FIG. 29.

An identification ink dot (mark) 605 (as shown in FIG. 30a) is placed on the potted surface above the central fiber at the proximal end of the formed body. The tension on the ends of the fibers is then released and the formed body is removed from the mandrels. The optical fibers are, preferably, made from polymeric material. The preferred UV curable adhesive (potting material) is ELC 4481 made by Electrolyte Corporation ("ELC"). The optical fiber, thermocouple wire, and the mandrels may be of different sizes. It is preferred that the overall cross sectional diameter of this fiber assembly at this point in the construction process be kept at or below approximately 600 um (microns) when 125 um diameter optical fiber is used. The thermocouple is preferably a type T thermocouple with wire and bead size of 2 and 8 mils, respectively.

Figure 30B:
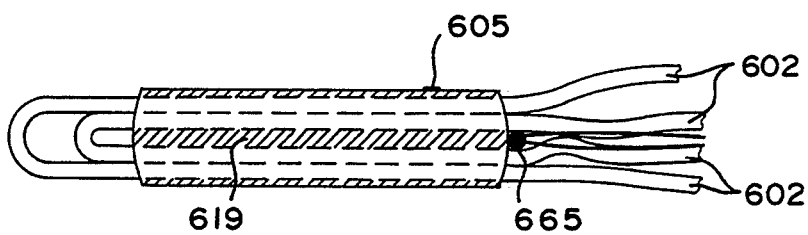
Figure 30C:
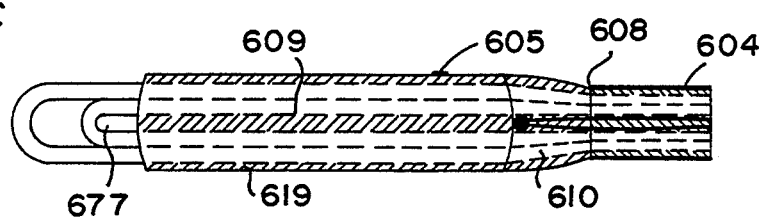
Figure 30D:
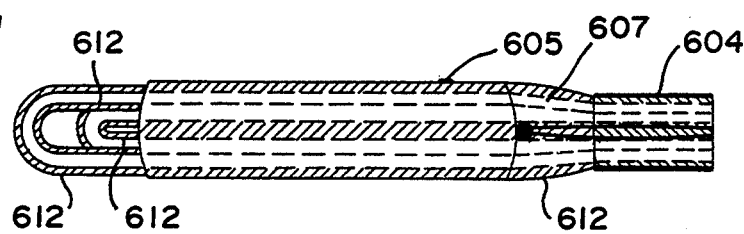
Figure 30E:
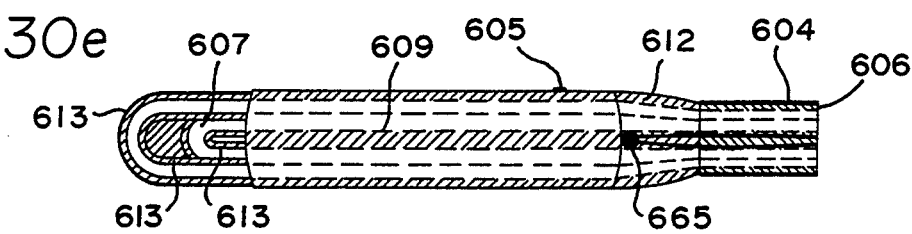
Figure 30F:
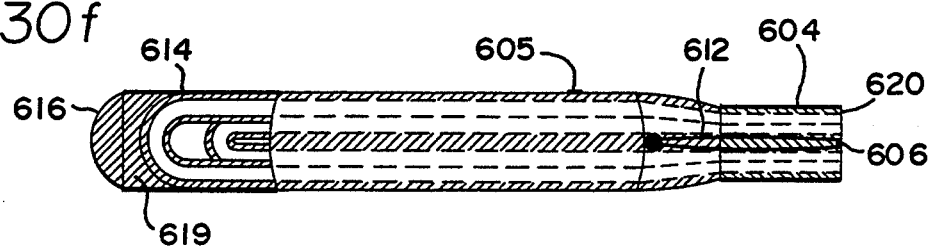

As shown in FIGS. 30a and 30b, a device according to one preferred embodiment of the present invention is made by producing a fiber assembly as previously described and creating a potted segment 619 on it and then placing the loose strands of the optical fibers 602 extending from the proximal end of the formed body in an opaque, thin wall, smooth surface, and flexible tube 604. The tube 604 is then filled with another adhesive 606 (e.g. Epotek 301 from Epoxy Technology Co.) to give that segment of the probe body an incremental structural strength. This extra strength is beneficial in a clinical situation when a probe body is inserted manually into an in-dwelling catheter, particularly one that is bent or curved in place. Prior-to emplacement of the tube 604, a thermocouple 665 is disposed among the fibers of the fiber assembly. Prior to the curing of the adhesive, the tube's distal end 608 is pushed against a tapered segment 610 of the proximal end of the formed body or fiber assembly 609. The tube 604 is most preferably opaque, e.g., but not limited to, black in color, and made from polyimide material. For this particular device the outside diameter along this segment is preferably about 500 um. The length of the polyimide tube 604 is preferably about 3 to about 6 inches. Different lengths are easily adapted for different applications. The relative reduction of the outside diameter of the portion with the tube in comparison to the diameter of the non-enclosed portion of the fiber assembly presents a significant advantage in a clinical application—the diameter of a portion of the probe body which is to be situated inside an in-dwelling catheter is minimized for increased or maximum flow of fluids including blood and/or pressure monitoring fluids through the catheter.

A portion 607 of the formed assembly protruding from the tube 604 is further coated with an amount 612 of the UV curable potting material (as in segment 619) to even up surface deformities and discontinuities between outer surfaces of the two portions. This step is performed preferably by an outward extrusion of the formed body through a precise metal orifice filled with the potting material. This step also adds potting material 612 at the bent portions of the fibers and it may slightly increase the outer diameter of the formed body; however, the surface finish is significantly improved. Bent portions of the optical fibers are thinly coated with this material, which protects the fibers from the harsh solvents contained in subsequent coatings. After this step, the outer diameter of the formed body approaches 650 um.

The probe body 609 is then dipped vertically in a solvent based opaque solution to uniformly coat the bent fibers portion 677 with a permanent opaque coating 613. This coating enhances or assures proper optical isolation of the transmitted light in the optical fibers 5 from the outside environment. The coating 613 also dramatically reduces the penetration of background and reflected light into the fibers and minimizes cross talk between the individual adjacent channels (fibers).

To further isolate and strengthen the portion 677 of the probe body 609, a short, thin wall, opaque tube 614 encapsulates and is bonded to the bent optical fibers using the same UV curable potting material as that for the segment 619. A smooth round shaped tip 616 (like the tips in FIGS. 11a and 23) is formed at the distal end of the probe body. Preferably the outer diameter of the tube 614 matches that of the formed body, to which it is bonded. The length of the tube 614 for this particular embodiment is about 0.100 inches and the tube is preferably made from polyimide material.

On the other end 620 of the probe body, loose optical fiber strands and a portion 622 of the polyimide tube are harnessed in a co-extruded flexible tubing 624, which is securely bonded inside a Y connector 626 on one end and to an integrated optical connector 628 on the other end. (see for example the connectors disclosed in issued U.S. Pat. No. 5,133,032 and pending U.S. application Ser. No. 07/782,557 filed Oct. 25, 1991, U.S. Pat. No. 5,159,654 both co-owned with the present invention and application). The optical connector provides an interface for a transmission cable 667 which connects the probe to an instrument such as a blood gas analyser 668. The Y connector 626 provides an interfacing port for liquid flow, such as the flow of blood and pressure monitoring fluids. In addition, the Y connector 626 also provides a luer fitting to mate to a catheter or cuvette fitting.

Figure 31:
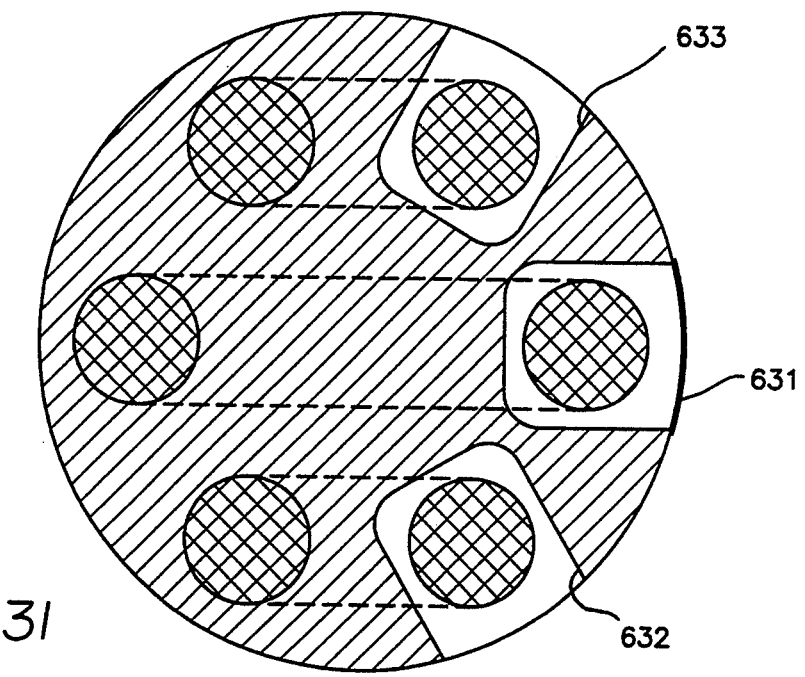
FIGS. 31 and 32 are end cross-sectional views of the probe of FIG. 30a at one stage of fabrication.
Figure 30G:
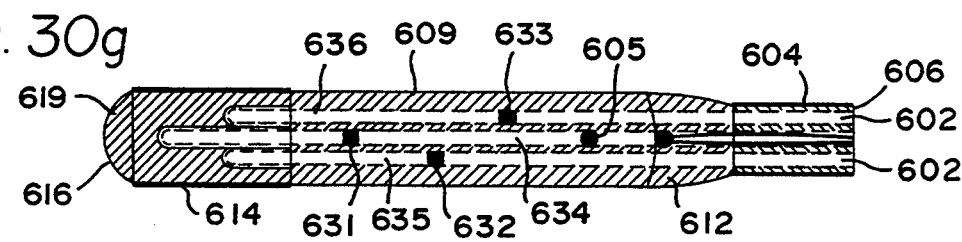

FIGS. 31–36 show longitudinal and cross sectional views of a probe body 609 after chambers 631, 632, 633 have been created in individual optical fibers 634, 635, 636. The location and the distribution of these chambers is, preferably, predetermined. An excimer laser or any equivalent means is, preferably, used to make these chambers in the probe body. The laser provides accurate geometry and smooth cut surfaces. The dimensions of the chambers are as desired and, preferably as described previously above; e.g., but not, limited to generally five-walled chambers with dimensions of about 150 um by 150 um by 100 um. Their preferable relative location for this particular embodiment is shown in FIGS. 30g and 31. Different chamber geometries and spatial distributions may also be employed. The chambers are preferably disposed and oriented so that when emplaced in an in-dwelling catheter they open in an upwards direction, (e.g. as discussed in pending U.S. application Ser. No. 07/774,693 co-owned with this application) for advantageous placement of the probe in a blood vessel. The ink dot 605 is used to facilitate alignment of the chamber 631, preferably an oxygen sensor, with the middle optical fiber 634.

Figure 32:
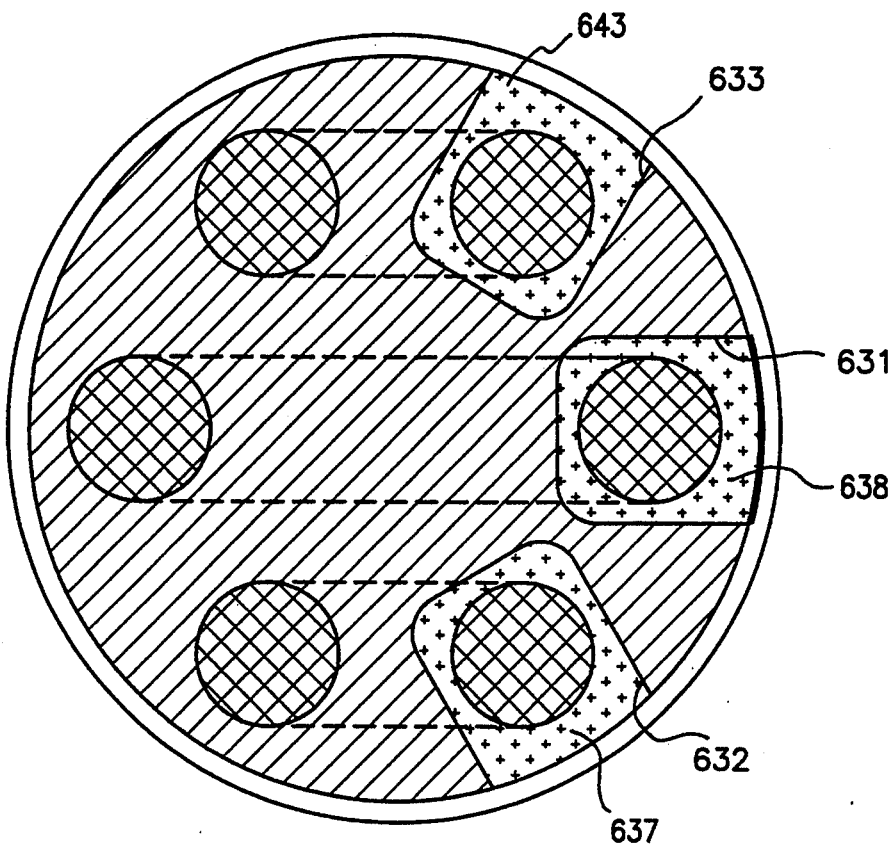

FIG. 32 shows a side view of the chambers after filling with an indicator complex. The filling process is preferably performed in a sequence-which takes into account certain material's physical and chemical characteristics and limitations. In addition, the steps and procedures taken are preferably optimized for higher fabrication efficiency and yields. First, the chamber 632 is loaded with pCO2 indicator complex 637. Second, the distal chamber 631 is loaded with pO2 indicator complex 638. A gas permeable membrane 639 (see FIG. 34) is uniformly applied on the filled pO2 chamber 631. The pCO2 filled chamber 632 is then rehydrated with a small amount of pCO2 support media. A similar gas permeable membrane 641 (see FIG. 33) is applied to the pCO2 chamber 632. These membranes are then permitted to cure in a humid environment to gain structural strength and to effect proper bonding to the probe surface. Then the chambers 631 and 632 are further coated with a second gas permeable membrane 642 (dip coat; see FIGS. 33 and 34) as the probe body is dipped in this coating. The dipping is only allowed to proceed slightly above the pCO2 chamber 632, and preferably not as far as the pH chamber 633. The probe is allowed to cure again in a humid environment. Third, the proximal chamber 633 (see FIG. 35) is loaded with a pH indicator complex 643. The filled chamber is then coated with a water permeable membrane 644 as the probe body, from the distal tip to the polyimide tube junction, is uniformly dipped in this material. An alternative water permeable patch membrane 645 (see FIG. 35) may be applied to the filled pH chamber 633. In one alternative embodiment the combination of a patch membrane 645 (as FIG. 35) and a dip coating 644 (as in FIG. 36) increases the structural integrity and adhesion of the patch membrane to the probe surface. To further increase the optical isolation of the probe body and the chambers, an opaque coating 647 is uniformly applied on the probe body. The opacity provided in this coating may also be incorporated in the water permeable coating 644; i.e., coating 647 and dip coating 644 may be combined in one material for coating which requires only one fabrication/dipping step. Finally, a thin and uniform anti-thrombogenic coating 648 is applied to the whole surface of the probe body, including the upper portions, the polyimide tube 604 and the Y connector 626, and preferably including all interior surfaces of the Y connector which come in contact with blood.

Incorporated fully herein by reference is the pending application entitled "Fiber-Optic Probe For The Measurement Of Fluid Parameters," filed on even date herewith and co-owned with this invention and application, a copy of which is appended hereto. Probe pH sample chambers (e.g. chamber 637) preferably have an indicator complex therein which comprises an absorbance dye such as phenol red covalently bonded to the surface of porous glass and made into a slurry or gel with hydrophilic polymer such as, but not limited to, hydroxy ethyl cellulose. A protective envelope of hydrophilic film or membrane over the chamber area maintains the indicator inside the chamber and acts like a selective hydrogen ion permeable membrane allowing hydronium ions to flow outside the probe and into the chamber. A hydrophilic opaque coating (e.g., but not limited to black or white in color) over the chamber area provides a protective layer to isolate the optical indicator from the environment which is being monitored. Additionally, this coating provides a suitable uniform smooth surface for the appliction of an anti-thrombogenic reagent preferably a heparine complex of benzalkonium chloride. Probe carbon dioxide sample chambers (e.g. chamber 632) are preferably filled with a carbon-dioxide-sensitive analyte indicator such as phenol red. This covalently bonded indicator is made into a gel form with a hydrophilic polymer having a desired concentration of bicarbonate to create carbonic acid inside the chamber after exposure to carbon dioxide. The formation of this acid is proportional to the amount of analyte gas interaction and the acid in turn reacts with indicator to change the color of the indicator present in the chamber. The chamber also has a gas permeable membrane cast over it along with an overcoating of a second hydrophobic film or membrane (preferably polyurethane) to provide additional strength and stability. An opaque coating over these membranes prevents or inhibits the loss of light and inhibits the interaction of light etc. from the outside environment with the chamber's contents. An anti-thrombogenic reagent covers the area of the carbon dioxide indicator chamber. Probe oxygen sample chambers preferably have an oxygen quenchable or sensitive fluorescent indicator dye, e.g. but not limited to a Ruthenium II compound which is placed inside the chamber. A semi-permeable gas membrane (e.g., but not limited to polydimethylsiloxane copolymer) is applied over the chamber which selectively permits oxygen to pass through the membrane and helps to maintain the indicator complex in the chamber. An additional layer of a hydrophobic, but gas-permeable, membrane(e.g., but not limited to, urethane) is cast over the sample chamber. Isolation of the chamber from the outside environment is provided by an opaque coating or membrane cast over the chamber.

Figure 37:
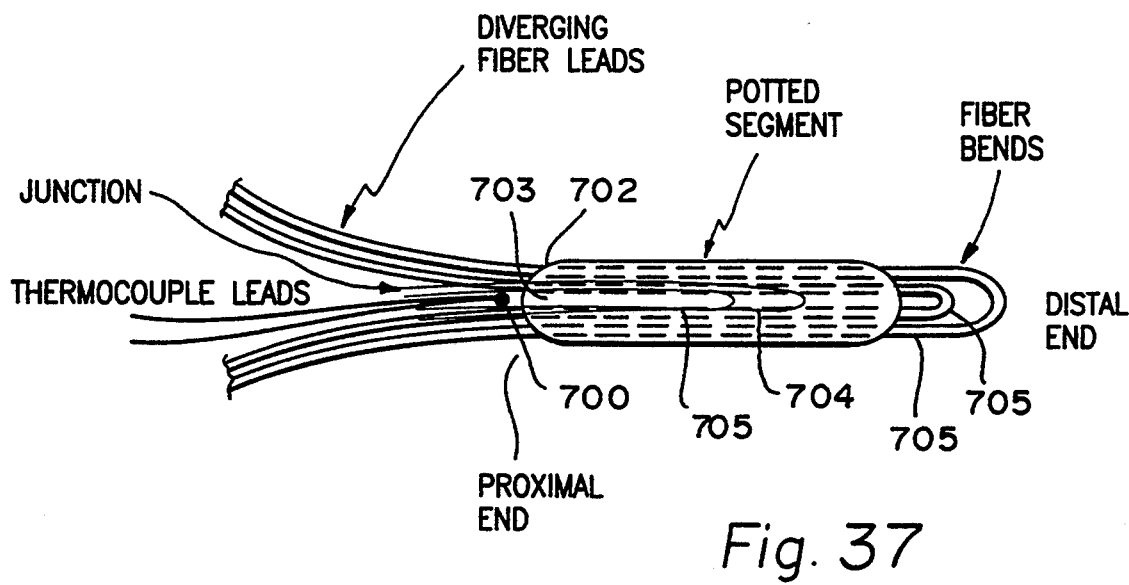
FIG. 37 is a top view of a fiber assembly according to the present invention.
Figure 33:
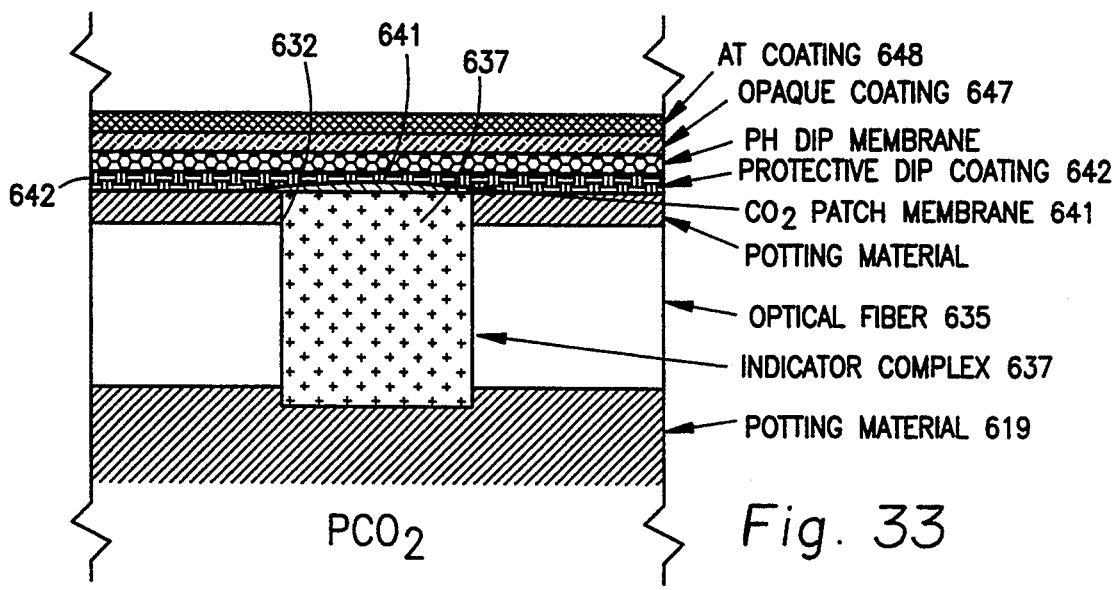
Figure 34:
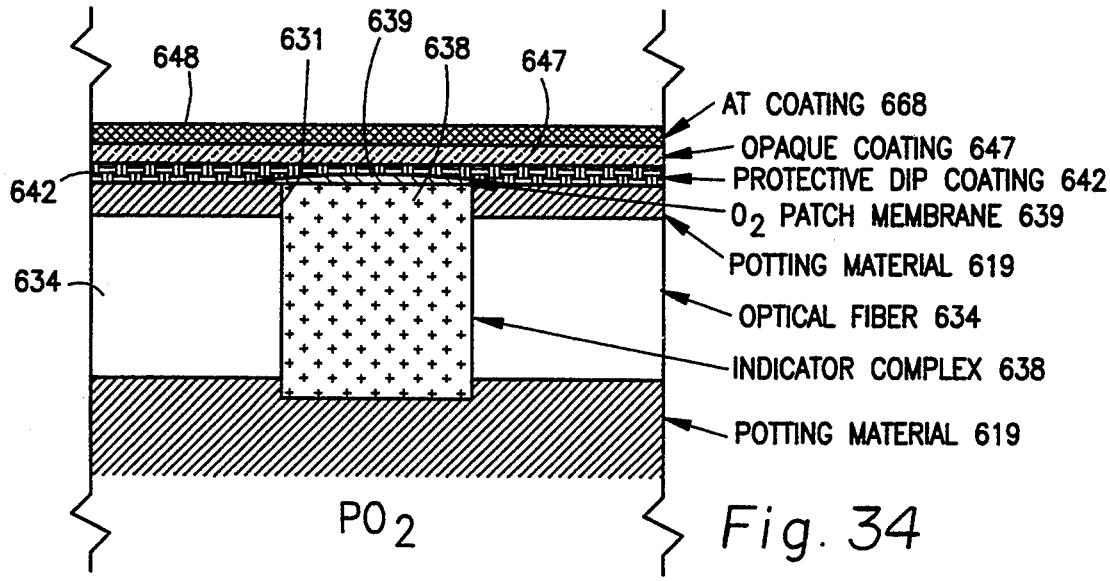
Figure 35:
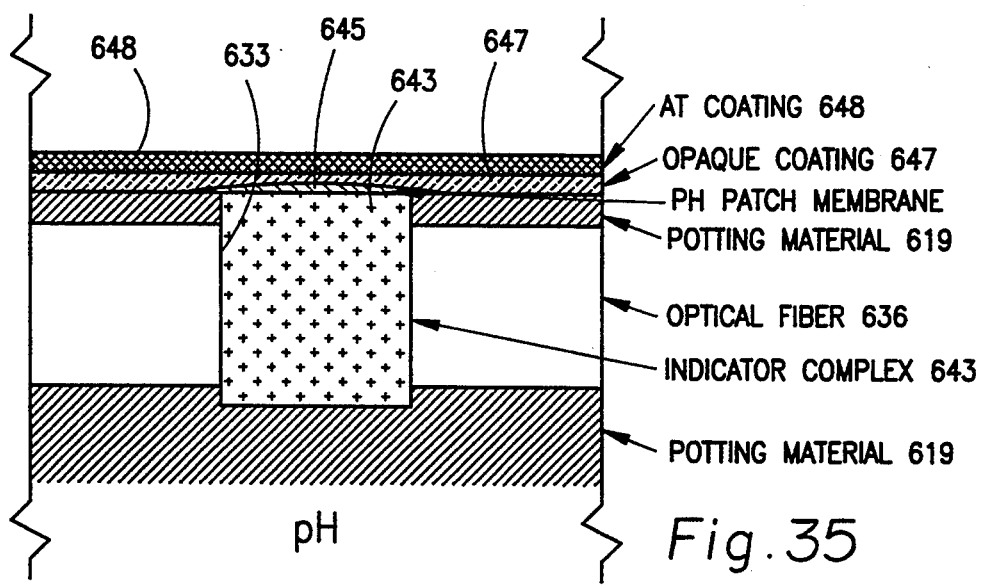
Figure 36:
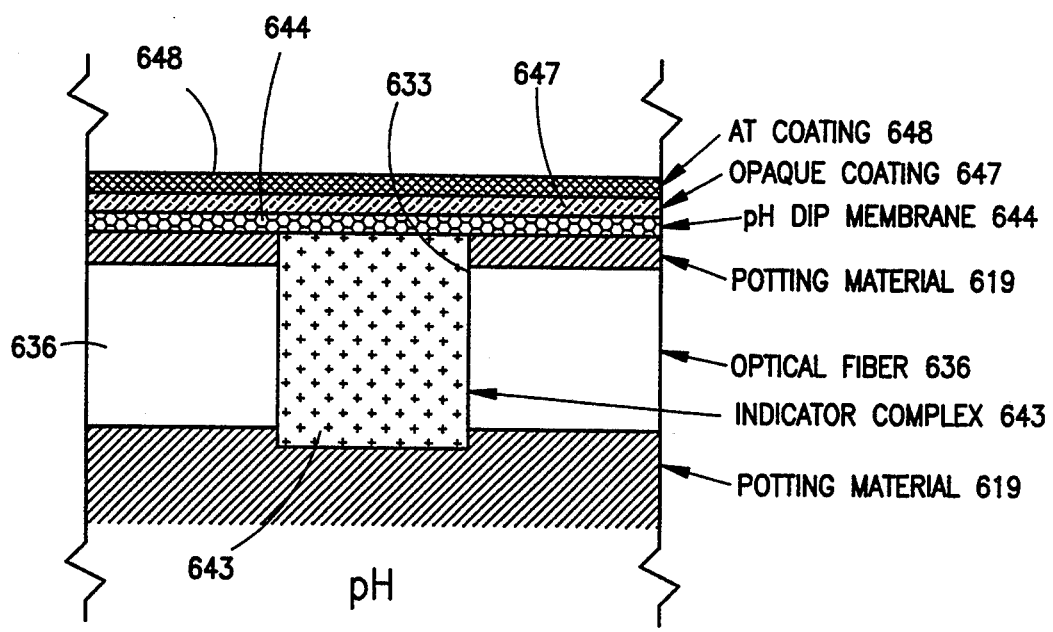

As shown in FIG. 37 a thermocouple 700 is integrated into a probe body 702 at a proximal end of a potted segment 703. The thermocouple junction is located proximally adjacent to the potted segment created in a fabrication and racking process as previously described herein. Three fibers 705 are suspended on the rack tooling in a parallel circular array, with preferably one-hundred-eighty-degree bends in the fibers at the distal end of the array. Potting compound 704 is applied in a cylindrical segment near the bends and is then cured solid by exposure to ultraviolet light. The resulting assembly 710 is removed from the rack and the potted segment is then clamped in a clamp or vise. The six fiber bends are separated into two generally symmetrical groups 707 and 708, diverging at the proximal end of the potted segment 703. This divergence is preferably maintained by fixtures. The thermocouple 700 is mounted in a pinch clamp, which is fastened to a slide which is disposed in a slide way. The thermocouple junction extends from the clamp while the parallel leads of the thermocuople are directly clamped about one centimeter from the junction. The thermocouple junction 711 is directed along the central axis of the potted segment by means of the pinch clamp, the slide, and the slide way. The thermocouple junction is precisely positioned proximal to the potted segment and centered in the circular fiber array. Screw threaded fixtures attached to the components aid in radial positioning and adjustable screws stops aid in axial positioning. When the thermocouple junction is in position, a small volume of potting compound 713 is applied to the thermocouple junction. The potting compound wets the junction and the fibers immediately surrounding the junction. The potting compound is cured by exposure to ultraviolet light, encapsulating the thermocouple junction, with the leads extending in the proximal direction parallel to the fibers. The leads and the fibers from this point are not potted to their ends.

For potting a fiber array hanging from a rack as previously described herein, it is preferred that an automatic potting method and devices be used. For example one or a plurality of symetrically disposed potting material pumps may be movably positioned about the fibers to apply a uniform amount of potting material automatically to the fibers. Preferably two such pumps are used with dies having a semicircular diameter which when combined equals the total desired diameter of a resulting fiber assembly. A motor drive the pumps in their movement along the fibers. Similarly, movable ultravioloet lights (one or more) are also movably mounted to move along the fibers after the potting material has been applied to cure it.

Figure 38A:
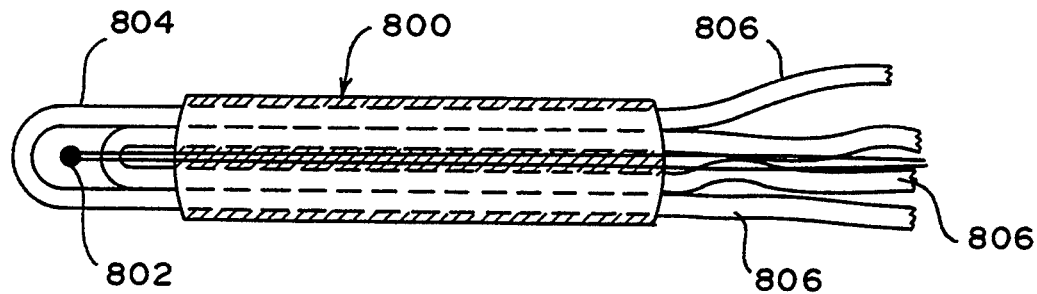
FIGS. 38a and 38b are side cross-sectional views of a probe according {0 the present invention.
Figure 38B:
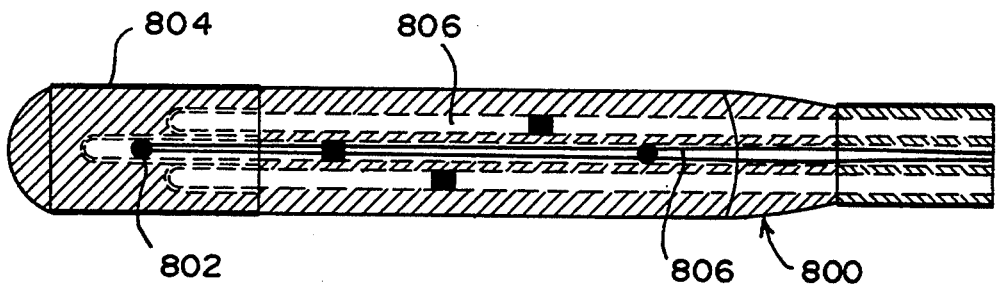

FIGS. 38a and 38b show an alternative preferred embodiment of a probe 800 according to the present invention in which initially in the fabrication process a thermocouple 802 is emplaced near an end 804 of the probe in the midst of several optical fibers 806. As shown in FIG. 38b the resulting probe is like the probe shown in FIG. 30g except for the location of the thermocouple 802.

In conclusion, therefore, it is seen that the present invention and the embodiments disclosed herein are well adapted to carry out the objectives and obtain the ends set forth at the outset. Certain changes can be made in the method and apparatus without departing from the spirit and the scope of this invention. It is realized that changes are possible and it is further intended that each element or step recited in any of the following claims is to be understood as referring to all equivalent elements or steps for accomplishing substantially the same results in substantially the same or equivalent manner. It is intended to cover the invention broadly in whatever form its principles may be utilized. The present invention is, therefore, well adapted to carry out the objects and obtain the ends and advantages mentioned, as well as others inherent therein.

What is claimed is:

1. A method for making an optical fiber sensor probe having a plurality of optical fibers, the method comprising aggregating together a plurality of optical fibers, certain of the optical fibers having a bend therein, the fiber bends disposed in a first section of the optical fiber probe near or at a first end of the optical fiber probe, the optical fiber probe having a second section adjacent the first section and a third section adjacent the second section, encapsulating the second section of the optical fiber probe in plotting material and curing the potting material, loose ends of the optical fibers extending from the second section and into the third section, emplacing a first tube over a portion of the third section of the optical fiber probe, and emplacing a second tube over the first section of the optical fiber probe.

2. The method of claim 1 wherein the first tube is opaque and flexible.

3. The method of claim 1 including also filling the first tube with adhesive to strengthen the optical fiber probe's third section.

4. The method of claim 1 comprising also prior to emplacing the first tube, disposing a thermocouple in the third section of the optical fiber probe, the thermocouple having thermocouple leads extending from the third section.

5. The method of claim 1 wherein the optical fiber probe's second section is larger in cross-section than the third section, the probe has a fourth section between the second and third section, and the fourth section tapers from the larger second section to the third section.

6. The method of claim 2 wherein the first tube is a polyimide tube.

7. The method of claim 1 wherein the second tube is a polyimide tube.

8. The method of claim 1 comprising also, prior to emplacing the second tube,
encapsulating optical fiber portions in the first section, including the fiber bends, with potting material and curing the potting material.

9. The method of claim 8 comprising also, prior to emplacing the second tube,
applying an opaque coating to the optical fiber portions in the first section, including to the fiber bends.

10. The method of claim 1 comprising also
forming a smooth round tip of potting material at an end of the first section distal from the second section, and curing the potting material.

11. The method of claim 1 comprising also
bonding the second tube to the first section of the optical fiber probe.

12. The method of claim 1 comprising also
harnessing loose optical fiber ends extending from the third section of the optical fiber probe and a portion of the first tube in a third flexible tube for connection to an optical fiber connector,
forming a gap in each optical fiber in the second section of the optical fiber probe, the gaps spaced apart from each other, and
installing a chemical analyte sensor in each gap.

13. The method of claim 12 comprising also
the plurality of optical fibers comprising three optical fibers, one gap formed in each of the optical fibers, each gap comprising a chamber,
installing a pCO2 indicator complex in a first chamber of a first optical fiber of the three optical fibers,
installing a pO2 indicator complex in a second chamber of a second optical fiber of the three optical fibers,
applying a curable first permeable membrane over the pO2 indicator complex,
applying a curable second permeable membrane over the pCO2 and allowing the first and second permeable membranes to cure,
applying a third curable permeable membrane covering both the pO2 and the pCO2 indicator complexes and allowing it to cure, then,
installing a pH indicator in a third chamber of a third optical fiber of the three optical fibers, and
applying a permeable membrane over the pH indicator complex.

14. The method of claim 13 comprising also
applying an opaque coating to the first, second and third sections of the optical fiber probe.

15. The method of claim 14 comprising also
applying an anti thrombogenic coating to the first, second, and third sections of the optical fiber probe.

16. The method of claim 1 comprising also
prior to encapsulating the second section, disposing a thermocouple in the first section, the thermocouple having thermocouple leads extending from the optical fiber probe.

17. The method of claim 1 wherein
a plurality of pairs of optical fibers are associated together,
each pair comprising a first and a second optical fiber, the first optical fiber having a bent portion disposed in the first section of the optical fiber probe and a portion extending into the second section of the optical fiber probe, and
the second optical fiber extending from the second section of the optical fiber probe into a third section thereof,
an end of the first optical fiber spaced part from an end of the second optical fiber in the second section of the optical fiber probe, space between the two ends suitable for receiving a chemical indicator.

18. The method of claim 12 wherein the permeable membranes are cured in a humid environment.

19. A method for making an optical fiber sensor probe having a plurality of optical fibers, the method comprising
combining three optical fibers, each having a bend therein, the bends disposed in a first section of the probe near a first end thereof,
the probe having a second section adjacent the first section, a third section adjacent the second section, the second section disposed between the first and third sections,
disposing a thermocouple with the three optical fibers, the thermocouple having thermocouple leads extending from the probe,
encapsulating the second section in potting material and curing it with loose ends of the optical fibers extending from the second section and into the third section,
emplacing an opaque flexible polyimide first tube over a portion of the third section and filling the first tube with adhesive to bond it to the third section and to strengthen the third section,
encapsulating optical fiber portions in the first section and the fiber bends with potting material and curing it,
applying a first opaque coating to the optical fiber portions in the first section, including to the fiber bends,
emplacing a second opaque flexible polyimide tube over the first section and bonding it to the first section,
forming a gap in each optical fiber in the second section, the gaps spaced apart from each other,
installing an analyte indicator complex in each gap, including installing a pO2 indicator complex in one gap, a pCO2 indicator complex in another gap, and a pH indicator complex in another gap.

20. The method of claim 19 comprising also
applying 2 permeable covering membranes over each indicator complex
applying a second opaque coating to the first, second, third, and fourth sections,
applying an anti-thrombogenic coating to the first, second, third and fourth sections, and
the second section larger in cross-section than the third section.

21. An optical fiber probe for sensing blood parameters, the probe comprising
a plurality of three optical fibers,
each optical fiber having a fiber bend therein and a gap therein, each gap containing an analyte indicator complex, one gap containing a pO2 indicator complex, another gap containing a pCO2 indicator complex, and another gap containing a pH indicator complex, the fiber bends and the indicator complexes encapsulated in cured potting material forming a probe body, the probe body covered with a permeable opaque first coating, each of the fiber bends covered with a permeable opaque second coating, a first opaque tube flexible polyimide bonded to the probe body and covering the fiber bends, a second opaque flexible polyimide tube covering loose ends of the optical fibers extending from the probe body, a thermocouple disposed in the probe body with thermocouple leads attached to the thermocouple and extending from the probe body, and an anti-thrombogenic coating over the probe body.

22. An optical fiber probe for sensing blood parameters, the probe comprising a plurality of three optical fibers, each optical fiber having a fiber bend therein and a gap herein, each gap containing an analyte indicator complex, one gap containing a $pO_2$ indicator complex, another gap containing a $pCO_2$ indicator complex, and another gap containing a pH indicator complex, the fiber bends and the indicator complexes encapsulated in cured potting material forming a probe body, the probe body covered with a permeable opaque first coating, each of the fiber bends covered with a permeable opaque second coating, a first opaque flexible polyimide tube bonded to the probe body and covering the fiber bends, a second opaque flexible polyimide tube covering loose ends of the optical fibers extending from the probe body, a thermocouple disposed in the probe body with thermocouple leads attached to the thermocouple and extending from the probe body, and an anti-thrombogenic coating over the probe body.

* * * * *